(12) United States Patent
Thurston et al.

(10) Patent No.: US 6,222,193 B1
(45) Date of Patent: Apr. 24, 2001

(54) RADIATION RESPONSIVE SURGICAL PROBE APPARATUS

(75) Inventors: Marlin O. Thurston; Karl W. Olson, both of Columbus, OH (US)

(73) Assignee: Neoprobe Corporation, Dublin, OH (US)

( * ) Notice: Subject to any disclaimer, the term of this patent is extended or adjusted under 35 U.S.C. 154(b) by 0 days.

(21) Appl. No.: 09/167,704

(22) Filed: Oct. 6, 1998

(51) Int. Cl.[7] .................................................. A61B 6/00
(52) U.S. Cl. ............................... 250/370.01; 280/370.13; 280/370.07; 280/336.1
(58) Field of Search .................... 250/370.01, 370.13, 250/370.07, 336.1

(56) References Cited

U.S. PATENT DOCUMENTS

| | | |
|---|---|---|
| 4,782,840 | 11/1988 | Martin et al. . |
| 4,801,803 | 1/1989 | Denen et al. . |
| 4,889,991 | 12/1989 | Ramsey et al. . |
| 4,893,013 | 1/1990 | Denen et al. . |
| 5,070,878 | 12/1991 | Denen . |
| 5,151,598 | 9/1992 | Denen . |
| 5,383,456 | 1/1995 | Arnold et al. . |
| 5,429,133 | 7/1995 | Thurston et al. . |
| 5,441,050 | 8/1995 | Thurston et al. . |
| 5,475,219 | 12/1995 | Olson . |
| 5,482,040 | 1/1996 | Martin, Jr. . |

OTHER PUBLICATIONS

Butler, et al., "Cd Zn Te Gamma Ray Detectors," IEEE Transactions on Nuclear Science, Santa Fe, N.Mex., 1991.
Doty, et al., "Properties of Cadmium Zinc Telluride Grown by a High Pressure Bridgeman Method," J. Vac. Sci Technology, vol. B10 Jun./Jul., 1992.
Butler, et al., "Recent Developments in Cd Zn Te Gamma Ray Detectors Technology," Proceedings of the International Symposium of the SPIE, Santa Fe, N.Mex., Jul., 1992.
Arnold, et al. "Radioimmunoguided Surgery in Primary Colorectal Carcinoma : An Intraoperative Prognostic Tool and Adjuvant to Traditional Staging," American J. Surg. 1995; 179: 315–318.
Schneebaum, et al., "The Significance of Introoperative Periportal Lymphnode Metostasis Identification in Patients with Colorectal Carcinoma," Cancer 1995; 75: 2809–2817.
Cote, et al., "Intraoperative Detection of Occult Colon Cancer Micronetosis using [125]I Radiolabeled Monoclonal Anti–body CC49," Cancer 1996; 77: 613–620.
Greenson, et al., "Identification of Occult Micrometastases in Pericolic Lymph Nodes of Dukes' B Colorectal Cancer Patients Using Monoclonal Antibodies Against Cytokeratin and CC49" Cancer 1994; 73: 563–569.
Bertsch, et al., "Radioimmunoguided Surgery System Improves Survival for Patients With Recurrent Colorectal Cancer," Surgery 1995; 118: 634–639.

Primary Examiner—Constantine Hannaher
Assistant Examiner—Andier Israel
(74) Attorney, Agent, or Firm—Mueller and Smith, LPA

(57) ABSTRACT

A hand-held surgical probe is provided with a crystal detector mount architecture wherein a rigid mounting of key components is achieved. In one embodiment, the crystal detector mount is supported and suspended by a vibration damping suspension externally located with respect to the crystal detector mount. The crystal detector mount architecture and vibration damping suspension act to reduce a variety of noise phenomena.

37 Claims, 10 Drawing Sheets

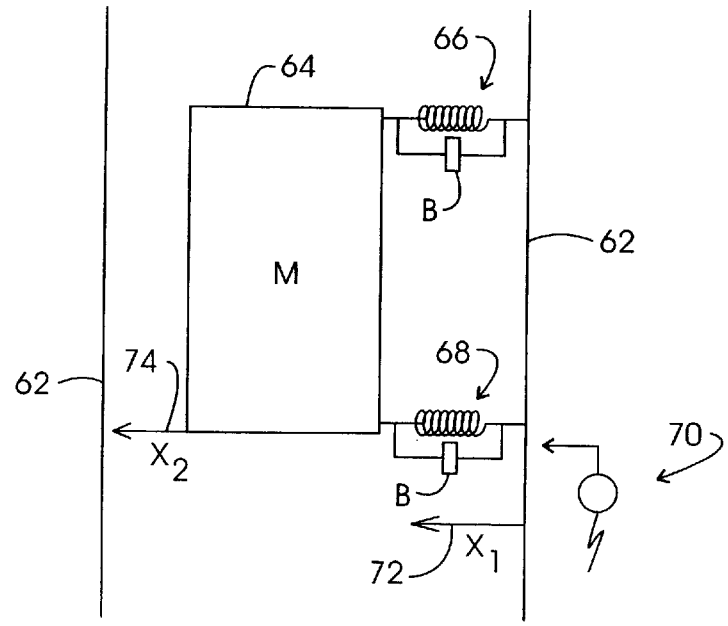
FIG. 2
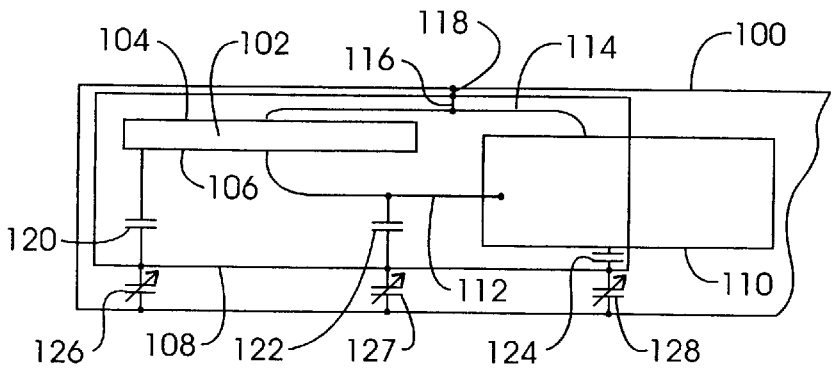
FIG. 3
PRIOR ART
FIG. 4

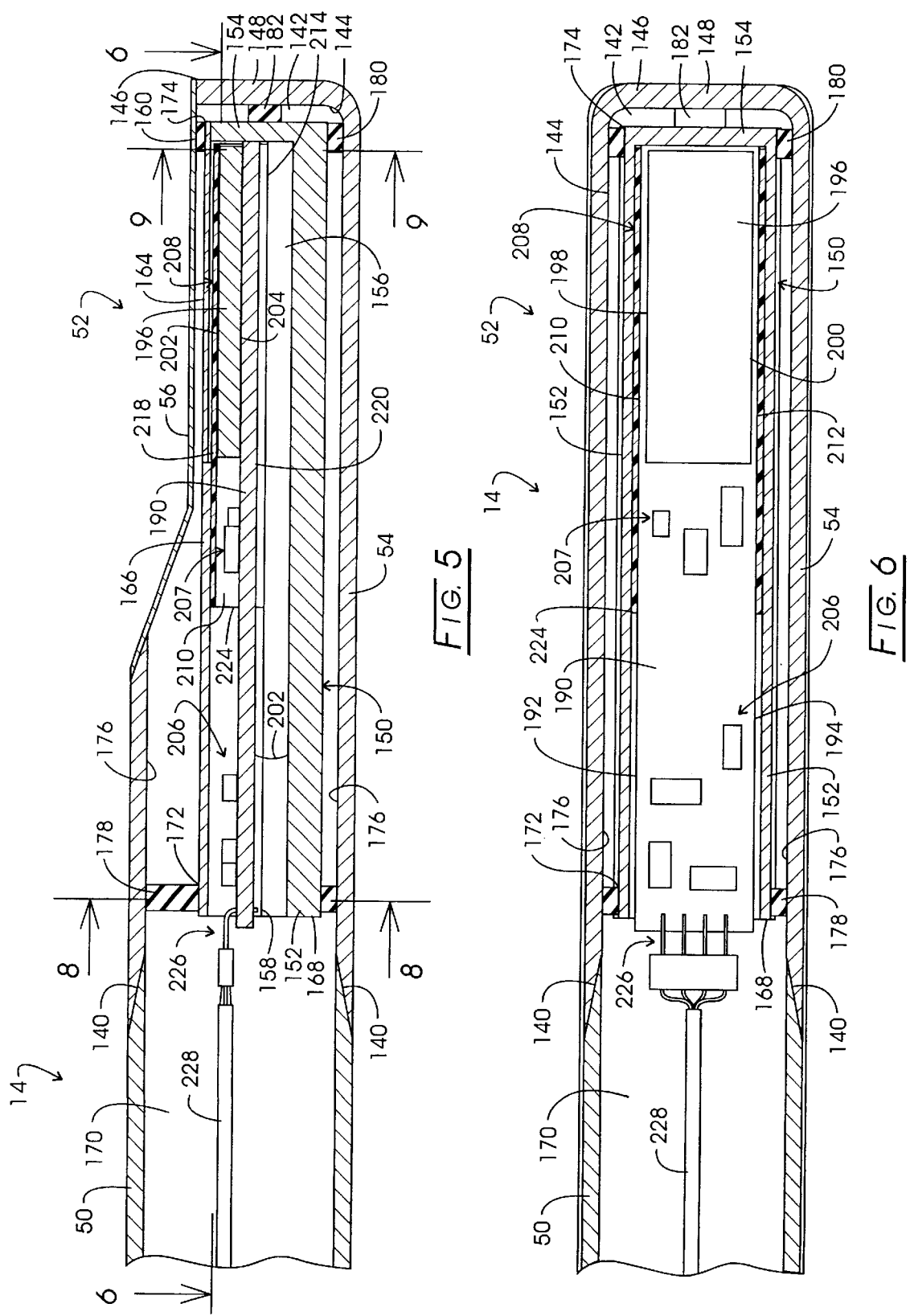

RADIATION RESPONSIVE SURGICAL PROBE APPARATUS

CROSS-REFERENCE TO RELATED APPLICATIONS

STATEMENT REGARDING FEDERALLY SPONSORED RESEARCH

Not applicable.

BACKGROUND OF THE INVENTION

Current and historical procedures for treatment of colon and rectal cancer generally have been based upon the natural history of tumor spread, and thence, upon operative and non-operative options available to the practitioner. Operative options generally have looked to the physical identification and surgical resection of tumor. A variety of techniques have been brought to bear in the art with the purpose of aiding the surgeon in detecting and localizing neoplastic tissue as part of this surgical procedure. ("Neoplastic tissue," for the present purposes, often is referred to as cancerous tissue, though malignant tumor and malignant tumor cells also are found in the terminology of the art. The term "neoplastic tissue" includes all of these.) A substantial amount of the effort which has been expended in seeking to aid the surgeon in the process of locating neoplastic tissue has been concerned with the utilization of radiolabeled antibody. For example, one technique includes the scintillation scanning of patients who have been injected with relatively high energy, e.g. $^{131}I$ labeled antibodies. Such photoscanning or scintillation scanning produces scintigrams which are difficult to interpret because of blood pool background radioactivity. Computer subtraction of radioactive blood pool agents and the use of two labeled antibodies (one specific for the tumor and one non-specific) have been attempted in an effort to enhance imaging. Nevertheless, such techniques have been found to provide little, if any, useful information to the surgeon, especially over and above the CAT scan, magnetic resonance imaging, and like traditional techniques. Typically, large tumor is readily located by the surgeon by visualization at the operating theater, and, in particular, through palpation, i.e. the feel of tumor as opposed to that of normal tissue. To achieve operative success, however, it is necessary for the surgeon to somehow locate "occult" tumor, i.e. tumor which cannot be found by the conventional surgical procedures of sight and feel. Failure to locate and remove such occult tumor generally will result in the continued growth of cancer in the patient, a condition often referred to as "recurrent" cancer. In general, conventional diagnostic techniques as, for example, use of the classic gamma camera and the like, fail to find or locate occult tumor. As tumor sites become smaller, the radionucleide concentrations at a given site will tend to be lost, from an imaging standpoint, in the background where blood pool radiation necessarily is present in the patient.

In 1984, Martin, M. D., and Thurston, Ph. D., introduced a much improved method for locating, differentiating, and removing neoplasms. Such technique uses a radiolabeled antibody and a portable radiation detection probe which the surgeon may use intraoperatively in order to detect sites of radioactivity. Because of the proximity of the detection probe to the labeled antibody, the faint radiation emanating from occult sites becomes detectable, for example, in part because of the inherent application of the approximate inverse square law of radiation propagation. The procedure now is known as radioimmunoguided surgery (RIGS®) (RIGS being a registered trademark of Neoprobe Corporation of Dublin, Ohio). The RIGS system for surgery additionally is successful because of a recognition that tumor detection should be delayed until the blood pool background of the circulating radiolabeled antibody has had an opportunity to be cleared from the body. As a consequence, the photon emissions or radiation emitted at minute tumors compared to surrounding tissue becomes detectable in view of the proximity of the probe device to it. Fortuitously, the radiolabeled antibody is capable of remaining bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand-held probe positioned in close proximity with the tissue under investigation. The seminal patent concerned with the RIGS procedure is U.S. Pat. No. 4,782,840 by Martin and Thurston, entitled "Method for Locating, Differentiating, and Removing Neoplasms," issued Nov. 8, 1988, and assigned in common herewith, the disclosure of which is expressly incorporated herein by reference.

The important advances achieved through radioimmunoguided-surgery have been reported. See in this regard, the following publications:

(1) "Radioimmunoguided Surgery System Improves Survival for Patients with Recurrent Colorectal cancer" Bertsch et al. *Surgery* 1995; 118: 634–639.

(2) "Radioimmunoguided Surgery in Primary Colorectal Carcinoma: An Intraoperative Prognostic Tool and Adjuvant to Traditional Staging," Arnold, et al. *American J. Surg.* 1995; 179: 315–318.

(3) "The Significance of Intraoperative Periportal Lymph Node Metastasis Identification in Patients with Colorectal Carcinoma," Schneebaum, et al. *Cancer* 1995; 75: 2809–2817.

(4) "Identification of Occult Micrometastases in Pericolic Lymph Nodes of Dukes' B Colorectal Cancer Patients Using Monoclonal Antibodies against Cytokeratin and CC49," Greenson, et al. *Cancer* 1994; 73: 563–569.

(5) "Intraoperative Detection of Occult Colon Cancer Micrometastases Using $^{125}I$-Radiolabeled Monoclonal Antibody CC49," Cote, et al., *Cancer* 1996; 77: 613–620.

The radioimmunoguided surgical system instrumentation is comprised generally of two basic components, a hand-held probe as described above, which is in electrical communication via a flexible cable with a control console. This control console is located within the operating room facility but out of the sterile field, while the hand-held probe and forward portions of its associated cable are located within that field. The hand-held radiation detecting probe is relatively small and performs in conjunction with a cadmium zinc telluride detector or crystal.

The hand-held probe and preamplification electronics mounted within it in support of the cadmium zinc telluride crystal have been the subject of extensive scientific development. Cadmium zinc telluride crystals are somewhat fragile and exhibit piezoelectric properties which, without rigorous accommodation, will produce deleterious noise phenomena and the like. Further, the crystal and its operatively associated preamplification function are called upon to detect necessarily very faint radiation. In this regard, only a very small amount of radioactive locator will be associated with minute, occult tumor. Thus, radiation emission count rates measured with the RIGS system are relatively low. A resultant operational criteria then requires a crystal geometry of adequately large surface area and a complementing preamplification function exhibiting the equivalent of an extremely high signal gain. Research activity in meeting the above operational criteria is reflected in the following U.S. Patents.

U.S. Pat. No. 4,801,803 by Denen, Thurston, and Ramsey, entitled "Detector and Localizer for Low Energy Radiation Emissions," issued Jan. 31, 1989.

U.S. Pat. No. 4,893,013 by Denen, Thurston, and Ramsey, entitled "Detector and Localizer for Low Energy Radiation Emissions," issued Jan. 9, 1990.

U.S. Pat. No. 5,070,878 by Denen, entitled "Detector and Localizer for Low Energy Radiation Emissions," issued Dec. 10, 1991.

U.S. Pat. No. 5,151,598 by Denen, entitled "Detector and Localizer for Low Energy Radiation Emissions," issued Sep. 29, 1992.

To derive data representing the presence or absence of occult tumor, a microprocessor-driven complex system of analysis continuously works to statistically evaluate validated counts or gamma strikes to aurally apprise the surgeon of the presence or absence of occult neoplastic tissue. An algorithm under which the noted evaluation takes place is described in U.S. Pat. No. 4,889,991 by Ramsey and Thurston, entitled "Gamma Radiation Detector with Enhanced Signal Treatment," issued Dec. 26, 1989.

The RIGS system, not only having demonstrated its value in locating occult neoplastic tissue, also substantially aids the surgeon in determining the proper staging of the patient in accordance with the extent and severity of the disease. Such staging aids in determining the appropriate post-surgical treatment of patients. In this regard, an effective staging technique utilizing the RIGS system has been described wherein an R Number is determined in accordance with the formula:

$$R \text{ Number} = (n_1 \times E_1)_1 + (n_2 \times E_2)_2 + (n_3 \times E_3)_3 + (n_4 \times E_4)_4$$

wherein each subscript 1–4 represents an anatomic zone, staging of the patient being based upon the R Number determination. See generally, Martin, Jr., U.S. Pat. No. 5,482,040, entitled "Biostaging of Adenocarcinomas Utilizing Radiolabeled Tumor-Associated Glycoprotein Antibodies," issued Jan. 9, 1996.

For many procedures, laparoscopic surgery (minimal access surgery) has become a desired alternative to traditional open surgery procedures. Particularly with the development of video-based visual systems, laparoscopic surgical techniques have been employed with more complicated gastrointestinal procedures. Such procedures look to savings in total health care costs as a result of shorter hospital stays and a more rapid patient return to normal activity. However, these procedures have required the development of instrumentation and techniques supplanting conventional three-dimensional viewing and tactile feedback to the surgeon.

In typical laparoscopic procedures, "space" for visualization by the surgeon via a video system, as well as for maneuvering laparoscopic instruments, is carried out in conjunction with a filling of the peritoneal cavity with a gas that distends the abdominal wall and provides an area for light and manipulation. This process is termed "pneumoperitoneum." Carbon dioxide currently is the standard gas used for pneumoperitoneum. Pneumoperitoneum typically is carried out utilizing an instrument referred to as an insufflator.

Laparoscopic surgical procedures generally feature the establishment of one or more portals of entry into the abdominal cavity. Mechanisms for inserting and removing various instruments through these portals without loss of pneumoperitoneum are necessary. These ports are established by the insertion of a trochar tip through the skin of the patient in conjunction with a port defining cannula or sheath. The trochar is inserted through the lumen of the cannula as an obturator. Typically the cannulas have an elastic valve to permit the introduction of instruments into the abdomen and prevent gas from escaping. Conventionally, the size of the cannula sleeve is 1 mm larger in diameter than the corresponding instrument that will traverse it. Diameters for such instruments may reach, for example, 15 mm, however, the surgical community prefers that the diameters of the instrument remain as small as possible.

The RIGS system has been introduced to laparoscopic surgery in connection with the surgical treatment of colorectal surgery. In a seminal patent concerning a laparoscopic probe instrument for carrying out the RIGS surgical system, the importance of a "side-looking" mounting of the cadmium telluride crystal is described. By utilizing such a crystal mounting, not only is the surgical procedure facilitated, but a crystal of adequate surface area may be used while the important diameter of the tubular-shaped instrument is maintained at a minimum value. See in this regard, U.S. Pat. No. 5,429,133 by Thurston and Slifko, entitled "Radiation Responsive Laparoscopic Instrument," issued Jul. 4, 1995. A diagnostic method for determining the treatment modality for neoplastic tissue within the peritoneal cavity of a patient utilizing a RIGS-based laparoscopic instrument is described in U.S. Pat. No. 5,383,456, by Arnold and Thurston, entitled "Radiation-Based Laparoscopic Method for Determining Treatment Modality," issued Jan. 24, 1995.

Developmental investigation of cadmium-telluride detector based probes has grown apace. Efforts looking to electrical noise phenomena avoidance have continued. Such endeavors have looked to noise sources and their accommodation. For example, scientific investigations now have revealed that probe designs should address a variety of noise inducing mechanisms accounting for the conversion of mechanical vibration to electrical pulses. These include the piezoelectric effect, the triboelectric effect and variations in capacitance between conducting surfaces. Prospective probe designs should remain amenable to practical manufacturing practices, as well as repairability features. In the latter regard, in their intraoperative environment of use, these very delicate instruments may be dropped or otherwise mishandled. In view of the continuing relatively higher cost of these instruments, such repair is of interest to the medical community.

Earlier probe architecture has sought to accommodate both the fragile nature and the piezoelectric reaction of cadmium-telluride-based crystal detectors with various forms of electrically conductive cushioning layers. Soft or yielding polymeric layers have been used where electrically insulative as well as electrically conductive properties have been called for. While a variety of these architectures have resulted in successfully performing probes, they have experienced manufacturing constraints. Additionally, the goal of evolving an advantageously heat sterilizable probe system has been an elusive one for investigators. However, probe mounted electronics have improved to the extent that some preamplifier circuits now will withstand the rigors of autoclaving. Further improvement has been called for in developing probe mounting structures which improve crystal detector performance but also which, of themselves, will withstand heat sterilization procedures.

BRIEF SUMMARY OF THE INVENTION

The present invention is addressed to an improved, hand-held surgical probe of a variety utilizing highly sensitive semiconductor crystal detectors, such as cadmium-telluride. Noise phenomena associated with such probes are identified to include the piezoelectric effect, noise inducement by a variation of capacitances, the triboelectric effect and electrostatic phenomena. To avoid or control these performance degrading phenomena, a crystal detector mount architecture is provided wherein a rigid mounting of key components is achieved. While a form of cushion support remains in one embodiment, it is externally located with respect to the crystal mount and is formed as a vibration damping spanned suspension.

Movement of key components within the probe creates variable capacitances which induce noise. The crystal mount architecture prevents such movement of the components, thus avoiding the deleterious noise. Rigid mounting of the key components is achieved by fixed attachment of such components to a crystal support and by way of a compressive, surrounding retainer and grounding assembly. Within the crystal detector mount is rigidly fixed a crystal support which is configured as a printed circuit board. A bias pad is formed on the printed circuit board which avoids noise generation otherwise caused by movement of the electrical leads. The crystal detector is rigidly connected to the printed circuit board over the bias pad. A close, compressive abutting contact of the bias pad and the crystal is achieved. Triboelectric charge generation, which is caused by the contact of dissimilar materials, is avoided since cadimium-telluride crystals are coated with a very thin layer of gold. By also coating the bias pad with a layer of gold, a resultant "gold-on-gold" contact prevents triboelectric charge generation. The components of the preamplification circuit are of the surface mount variety which prevents their displacement at the printed circuit board with respect to surrounding grounded surfaces.

The crystal detecting mount architecture provides a compressive, surrounding retainer and grounding assembly. Such assembly further prevents motion of the crystal detector, preamplification circuit and bias function with respect to the grounded probe housing. In one embodiment, the retainer and grounding assembly extends to cover the sensitive forward or charge accumulating stage of the preamplification circuit providing electrical shielding. In addition, the retainer and grounding assembly serves to electrically ground the forward face of the cadmium-telluride crystal, the crystal mount and the preamplification circuit.

A form of cushion support remains but is externally located with respect to the crystal mount. The cushioning support is provided by way of a vibration damping spanned suspension consisting of forward and rearward damping mounts. These mounts act to reduce vibration phenomena asserted at the probe's outer walls. The forward and rearward mounts are spaced a span or bridging distance apart to reduce noise caused by the piezoelectric nature of Cadmium-Telluride crystals.

Other objects of the invention will, in part, be obvious and will, in part, appear hereinafter. The invention, accordingly, comprises the system and apparatus possessing the construction, combination of elements, steps and arrangement of parts which are exemplified in the following description.

For a fuller understanding of the nature and objects of the invention, reference should be had to the following detailed description taken in connection with the accompanying drawings.

BRIEF DESCRIPTION OF THE DRAWINGS

FIG. 2 is a stylized representation of a vibration damping mount for a mounting component employed with the invention;

FIG. 3 is a stylized drawing of a crystal and preamplification stage mounting of the prior art;

FIG. 4 is a stylized drawing of a crystal detector and preamplification circuit mounting of the invention;

FIG. 5 is a partial sectional view taken through the plane 5—5 in FIG. 1;

FIG. 6 is a partial sectional view taken through the plane 6—6 in FIG. 5;

DETAILED DESCRIPTION OF THE INVENTION

Figure 1:
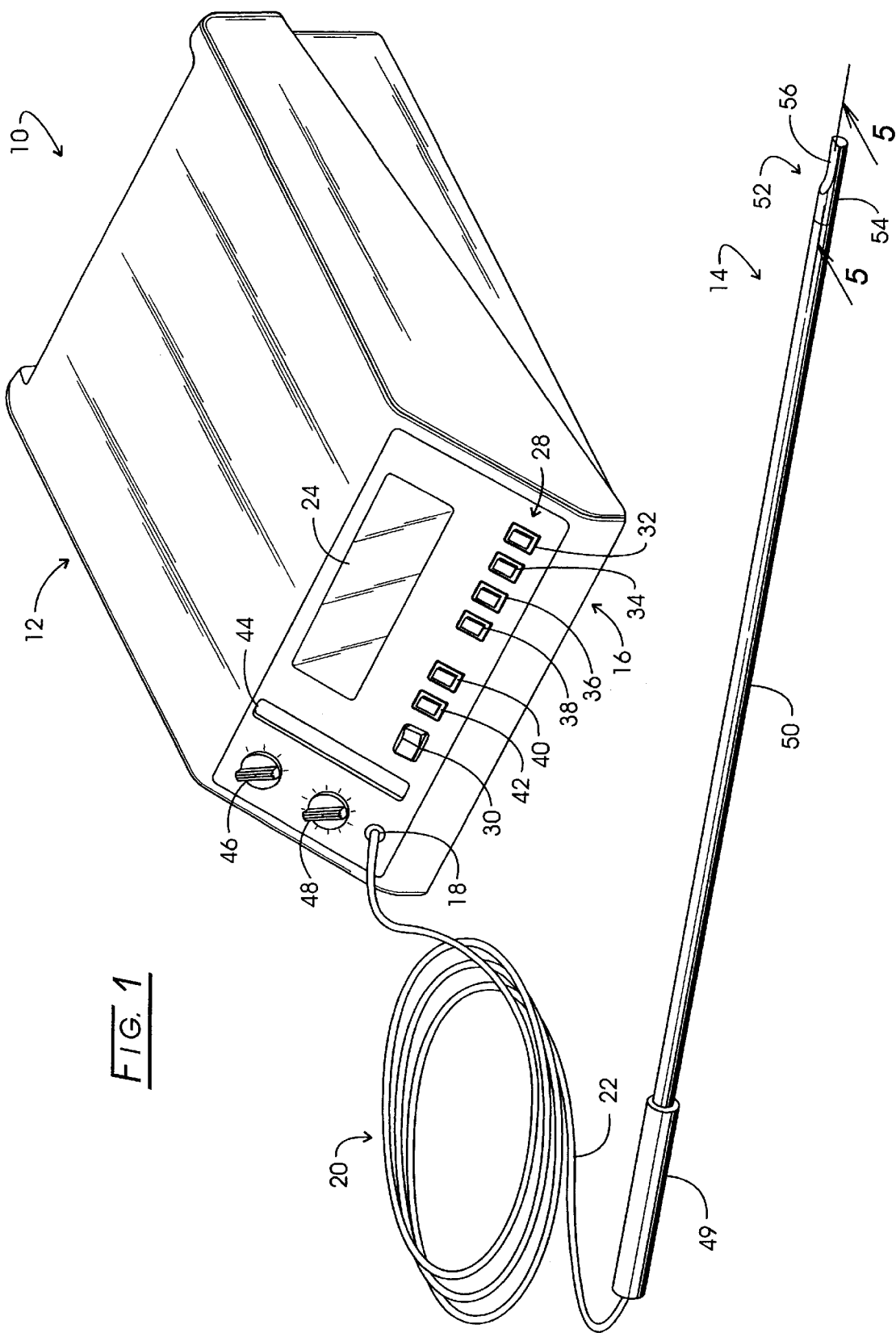
FIG. 1 is a pictorial representation of the system and instrumentation of the invention, showing a laparoscopic probe apparatus and embodiment.

In the discourse to follow, the hand-held surgical probe apparatus of the invention will be seen to be configured preferably with a cadmium-telluride crystal architecture and crystal biasing and grounding arrangement. In the latter regard, the forward face of the room temperature crystal detector is maintained at electrical ground, while a select bias voltage is applied to the rearward face. Thus configured, the crystal detectors perform in conjunction with a preamplification treatment circuit. Such circuits, for example, are described in U.S. Pat. No. 5,441,050 by Thurston and Olson entitled "Radiation Responsive Surgical Instrument." The preamplification circuits which are employed with the cadmium-telluride crystals are formed with a charge accumulation network and amplification stages. The charge accumulation network typically will include a coupling capacitor, a field effect transistor and a bias resistor. This stage performs with what may be considered an enormous effective gain. As a consequence, the most minute generation of electrical noise or electrical phenomena, not representing a photon event based signal of interest will have an adversely profound effect in the performance of the handheld probe and the control system with which it is associated. The noise phenomena addressed by way of probe structuring in the instant discussion will be the well known piezoelectric response of cadmium-telluride crystals; triboelectric charge generation which results from the relative motion of dissimilar materials; intra-component capacitance; and electrostatic phenomena. The architecture described performs in conjunction with probes which are intended for radioimmunoguided laparoscopy and open surgery; as well as lymph node mapping, calling for response to higher gamma energy.

CdTe crystals may be alloyed and still are referred to as "cadmium telluride" or "CdTe" crystals for present purposes. A preferred cadmium telluride crystal, as described in commonly-assigned U.S. Pat. No. 5,441,050, issued Aug. 15, 1995, is CdTe material alloyed with zinc and generally represented by the expression: $Cd^1{}_xZn_xTe$. In general, CdTe detecting crystals exhibit benefits such as operability at room temperature, high counting rates and small size. The proportioning of the Cd component and Zn component of the crystals may vary to provide an effective ratio selected to suit the particular requirements of the user. However, a lower limit or boundary for the proportion of zinc wherein x equals about 0.2 has been determined. Information concerning the alloyed crystals is provided in the following publications:

Butler, Lingren and Doty, "$Cd_{1-x}Zn_xTe$ Gamma Ray Detectors," IEEE Transactions on Nuclear Science, Santa Fe, N. Mex., 1991.

Butler, Doty and Lingren, "Recent Developments in CdZnTe Gamma Ray Detector Technology," Proceedings of the International Symposium of the SPIE, Santa Fe, N. Mex., July, 1992.

Doty, Butler, Schetziaa and Bowers, "Properties of Cadmium Zinc Telluride Grown by a High Pressure Bridgman Method," J. Vac. Sci. Technol., Vol. B10, June/July, 1992.

Referring to FIG. 1, a surgical system employing the features of the invention is represented generally at 10. System 10 includes a control assembly or console represented generally at 12 to which is coupled a probe instrument represented generally at 14. Probe 14 is a laparoscopic instrument intended for carrying out radioimmunoguided surgery (RIGS). Probes of different design are employed with the console 12 for the purposes, for example, of carrying out the RIGS procedure in conjunction with open surgery or for carrying out lymph node mapping with higher energy radionuclides. In the latter regard, the photon count evaluation, including lower threshold validation or windowing, and discriminator functions of the RIGS system are commonly utilized. The forward face 16 of console 12 includes a coupling or connector 18 which provides for electrical signal communication and power supply association with the probe instrument 14 via a transmission assembly represented generally at 20 which includes a flexible cable 22. This cable implementation of the transmission assembly is a preferred arrangement for such transmission functions, however, other approaches will occur to those skilled in the art. Forward face 16 of console 12 additionally carries a relatively large liquid crystal display (LCD) or readout 24, as well as an array of push-type switches 28. This array of switches permits the microprocessor driven control system 12 to carry out an instructive or "user friendly" dialogue with the practitioner. In addition to a conventional on and off rocker switch 30, the switches provided at forward face 16 include such function selection switches as a count mode switch 32, a reset count switch 34, a background count or squelch switch 36, a sound control switch 38, and down and up incrementing switches shown respectively at 40 and 42.

Also mounted at the forward face 16 of console 12 are components dedicated to the lymph-tracking features of the system 10. In this regard, a linear, segmented LED array 44 is included for the purpose of providing a visual cuing aspect as to peak count rate level. A range selection switch is provided at 46. Switch 46 permits the practitioner to select any of five count ranges to achieve full scale readouts. These ranges may, for example, be 0–100 counts per second; 20–1,000 counts per second; 50–2,500 counts per second; 100–7,500 counts per second; and 600–30,000 counts per second. Below the knob actuated range switch 46 is a knob actuated threshold control 48 which is used to provide a count rate threshold input which is a percentage evaluation of any one of the count rate ranges established at 46. This thresholding is a variation of the background count or squelch procedures carried out in connection with switches 36 and 34. In this regard, the function of reset count switch 34 is to derive a count value over a preset interval, for example, two seconds. The background count switch 36 is employed in conjunction with reset count switch 34 to develop a statistical count value based upon a measured background count rate. For example, in the RIGS procedure, targeting agent is systemically injected into the patent and the probe instrument 14 initially is positioned in the vicinity of the heart or aorta in order to obtain a blood pool background count rate. The interval during which this rate is determined is, for example, five seconds. The microprocessor-based control system 12 then calculates a statistically significant value, for example, a predetermined number of standard deviations of the basic count rate, to derive a statistically significant threshold radiation count rate level. This, for example, may be three sigma above the base count rate. The ranging procedure is referred to by surgeons as "squelching." Operating in conjunction with that threshold level in the RIGS procedure, the system 10 provides the surgeon with audible cues indicating that a high probability of tumor involvement is present at a location closely adjacent the position of the window of probe instrument 14. Not shown in FIG. 1 is a mode selection switch which is manually actuated between two positions, one electing that system 10 operate in a standard RIGS mode, and the other electing that the system 10 operate in conjunction with an adjunct system for carrying out sentinel node detection procedures and the like. Laparoscopic probe 14 is seen to include a hand-grippable base portion or region 49 having a rearward connector (not shown) coupled to cable 22. From that base portion for handle 49, an elongate accessing tube 50 extends to a tip region represented generally at 52. The tip region 52 includes an outer wall 54 which encloses a tip region cavity (not shown) having a periphery at which a side-looking radiation transmissive window 56 is provided. In general, the probe 14 is utilized in the manner described in the above referenced U.S. Pat. No. 5,383,456 by Arnold and Thurston.

The probe embodiment of the invention, including probe 14, employs an electrically conductive radiation attenuating crystal mount which serves to position the forward face of the cadmium-telluride crystal in spaced adjacency with respect to radiation transmissive window as at 56. To accommodate for externally induced vibrations, this crystal mount is suspended within a housing cavity, such as the noted tip region cavity, by vibration damping mounts. This arrangement is represented in stylized form in FIG. 2. Looking to that figure, the sidewalls of the outer housing of the probe structure are represented by lines 62. A crystal mount is represented by the block 64 which is shown having a mass, M. Mass M is illustrated being suspended from the outer housing wall 62 by two, spaced apart vibration damping mounts represented at 66 and 68. Mounts 66 and 68 are each shown as a combined spring and damper, B. The damped spring-like mounts are spaced apart a bridging or span distance. An application of mechanical vibration to the wall 62, as represented at symbol 70, will evoke a displacement, $x_1$, of the wall 62 as represented at arrow 72. If the mass, M, represented at 64, were equal to zero, the resultant movement of mass 64 as represented at arrow 74 and value $x_2$ would be equivalent to the value $x_1$. However, that displacement is reduced firstly in the presence of a real value of mass, M, and, secondly, by the damping feature, B, of the vibration damping mounts 66 and 68. In general, the mounts 66 and 68 are implemented by a closed cell polymeric foamaceous material.

Looking to FIG. 3, the approach generally utilized heretofore, wherein the cadmium-telluride crystals are mounted within a cushion layer in adjacency with a printed circuit board carrying a preamplifier, is stylistically illustrated. For this arrangement, both the crystal mount and the outer wall of the probe tip region are connected as represented by the outline 76. The cadmium-telluride crystal is represented by block 78. Crystal detector 78 is stylistically shown mounted upon compression springs 80 and 82 which, in general, has been implemented in the form of cushioning layers and resilient or relatively soft polymeric materials. The preamplifier function is typically implemented by a printed circuit and represented at block 84. From that preamplification circuit, an electrical lead extends as represented at line 86 to apply a voltage bias to the inward face 88 of the crystal detector 78. Correspondingly, a system ground is applied to the forward face 90 of crystal detector 78 as represented by line 92. The housing and metal crystal mount represented by outline 76 will be maintained at system ground.

With the voltage bias extent at inward face 88 of the crystal detector 78, any movement of the cushion mounted detector 78 will evoke a variation of capacitance established between that biased face and ground represented at outline 76. Such inner component capacitance variation is represented by the variable capacitor symbol 94 and the associated line extending from inward face 88 of crystal detector 78 and grounded sidewall 76. Correspondingly, any movement of those electrical circuit components such as represented at line 86, which deliver the bias input to inward face 88, will similarly result in the development of a capacitance variation as represented by variable capacitor symbol 96 and the line associated therewith extending from bias line 86 to the adjacent grounded surface represented at line 76. The bias voltage delivered to a bias resistor positioned upon the printed circuit as supported at 84 similarly will evolve a capacitance variation as represented by the variable capacitor symbol 98 and the associated line extending between block 84 and outline 76. These variable capacitance phenomena 94, 96 and 98 will be witnessed by the highly sensitive integrating front-end stage of the preamplifier circuit mounted at 84 and will result in noise phenomena for the system. Thus, while the cushioning layers protect the cadmium-telluride crystals from piezoelectric induced noise to a substantial extent, the capacitance variation induced noise remains problematic.

Now referring to FIG. 4, a stylized drawing is provided showing the precepts of the probe structures according to the invention. In the figure, the outer housing wall of a probe structure is represented by the outline 100. A detector crystal is represented at block 102 having a forward face 104 and an inward face 106. Crystal detector 102 is rigidly mounted to an inwardly disposed suspended electrically conductive and radiation attenuating crystal mount represented by block 108. This rigid mounting is through a similarly rigidly mounted, electrically insulated component (not shown) fixed to the mount 108. Additionally, fixed rigidly upon that electrically insulated component, is at least a forward charge collecting or integrating stage of the preamplification circuit represented at block 110. In this regard, the block outline of the crystal mount 108 is seen to extend over the front portion of block 110. Bias delivery, represented by line 112, also is rigidly fixed to the noted electrically insulative component. Instrument or system ground, as represented at line 114, not only is directed to the forward face 104 of crystal detector 102, but specifically is coupled to the electrically conductive crystal mount as represented by line segment 116. Additionally, this ground is connected to the outer housing as represented at outline 100 and line segment 118.

With the arrangement shown, the crystal mount assembly 108 is afforded control movement within the outer housing 100 as discussed in connection with FIG. 2. However, there is no relative motion between the biased face 106 of crystal detector 102 and the electrically conductive crystal mount 108. Accordingly, no capacitance variation can be generated to evoke noise, and this condition is represented by the fixed capacitor symbol 120 and the associated line leading from inward face 106 of crystal detector 102 and the electrically conductive crystal mount represented at 108. In similar fashion, the technique for applying bias from the forward portions of the preamplification function is a rigid coupling and no availability is present for a variation or movement to occur between the biasing function 112 and crystal mount 108. Accordingly, no capacitance variation generated noise is developed as represented by the fixed capacitor symbol 122 and the associated line extending from the bias delivery at line 112 and the crystal mount represented at 108. In similar fashion, because the forward stage components of the preamplification circuit 110 are fixed rigidly upon the mount 108, all be it through a similarly fixed rigid insulative support, no capacitance variation can be generated between the bias delivery components of the circuit and the grounded crystal mount 108. This relationship is represented by the fixed capacitor symbol 124 and the associated line extending between block 110 and block 108.

Permitted movement between the electrically conductive crystal mount 108 and the outer wall represented at boundary 100 might evoke a capacitance variation phenomena as represented by the variable capacitor symbols 126–128 and their associated connector lines between the mount block 108 and the housing represented at outline 100. However, because each of these components is specifically coupled to system ground, capacitance variation cannot produce a charge which could enter the preamplifier input. Thus, no noise is generated to disturb the preamplification input stage.

Referring to the FIGS. 5–7, the probe 14 laparoscopic implementation of the noise-avoidance features discussed in connection with FIG. 4 are revealed in detail. In the figures, the electrically conductive outer wall 54 of instrument 14 at tip region 52 reappears. This wall 54 has a generally cylindrical shape and is coupled to the accessing tube 50, for example, utilizing an electrically conductive epoxy adhesive at the union represented at line 140. Wall 54 functions to establish a tip region cavity 142 having side portions or inside surface of generally cylindrical configuration which extend to a generally rectangular periphery 146 extending rearwardly from the integrally formed front wall 148. Thus, the cavity 142 is configured in "side looking" fashion to improve the utility of instrument 14. The tip region cavity 142 is enclosed at the periphery 146 by the thin, radiation transmissive aluminum window 56.

Suspended within the "side looking" tip region cavity 142 is a mounting component represented generally at 150. Component 150 is formed of an electrically conductive material such as tungsten, lead or brass. In the latter regard, the probe 14 is used only with relatively low gamma energy radionuclides, and the latter material functions as an effective attenuator of the radiation encountered. Mount 150 is configured having generally cylindrically shaped side portions or walls 152, including an end wall 154 which define a mount cavity 156 (FIGS. 5 and 7).

Figure 8:
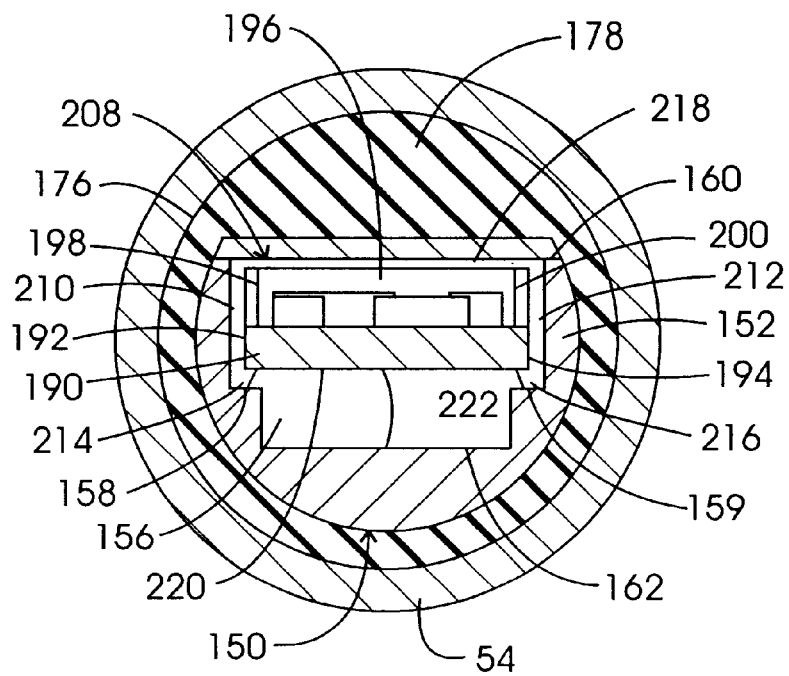
FIG. 8 is a sectional view taken through the plane 8—8 in FIG. 5.
Figure 9:
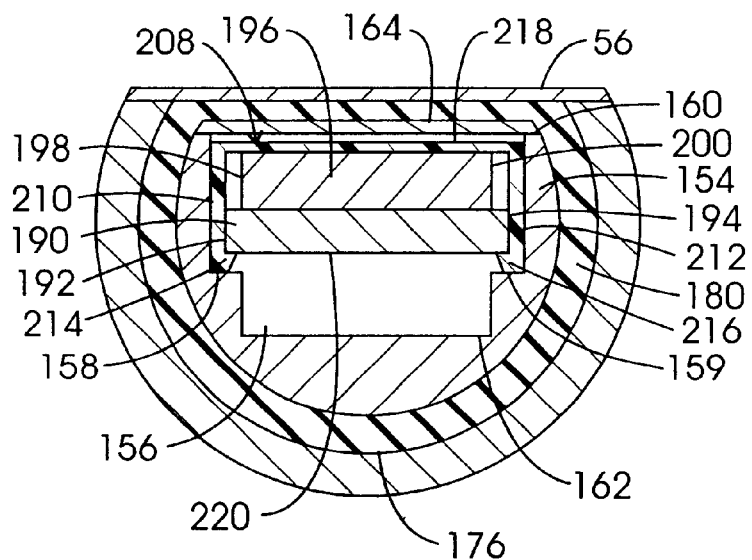
FIG. 9 is a sectional view taken through the plane 9—9 in FIG. 5.

Looking additionally to FIGS. 8 and 9, formed within the cavity 156 at the mount wall 152, are oppositely disposed flat elongate ledges 158 and 159. These ledges 158 and 159 are coplanar and in parallel with the rectangular periphery 160 of the mount cavity 156. Note that ledges 158–159 are positioned outwardly of the bottom surface 162 of cavity 156.

Figure 7:
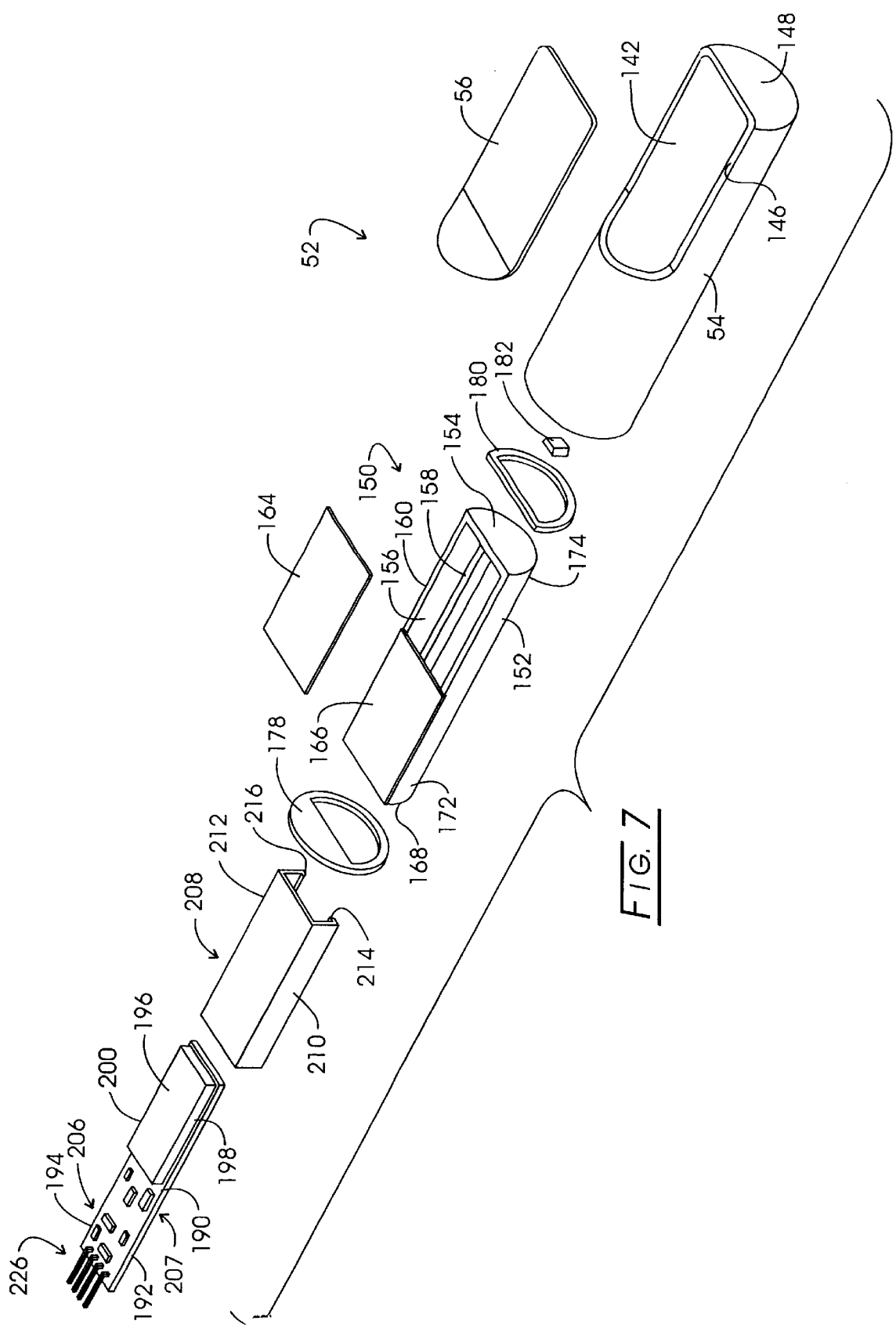
FIG. 7 is an exploded view of the probe tip region shown in FIGS. 5 and 6.

At the portion of mount periphery 160 adjacent the window 56 is the radiation transmissive aluminum foil cover 164 (FIGS. 5 and 7). Extending rearwardly from the foil cover 164 and fixed to the edge or periphery 160 is a metal, radiation attenuating, electrically conductive rectangular cover 166. Thus, the mount cavity 156 essentially is enclosed with the exception of being rearwardly open at end surface 168. In this regard, the cavity 156 communicates with a cavity 170 defined by the tubular nature of accessing tube 50.

In keeping with the discussion above in connection with FIG. 2, the mounting component 150 has spaced apart support portions 172 and 174. Portions 172 and 174 are longitudinally spaced apart a mount or bridging distance which, for the present embodiment, is somewhat coextensive with the forward tip region 52. Coupled between the support portion 172 and the inside surface 176 of outer wall 54 is a rearward vibration damping mount 178. The shape or profile of the vibration damping mount 178 is revealed in FIGS. 7 and 8. The mount 178 is of relatively thin dimension so as to provide an engagement with mounting component 150 which is finite and of limited extent.

In similar fashion, the forward edge of the mounting component 150 is supported from and suspended from interior surface 176 of wall 54 by a forward vibration damping mount 180. The profile of vibration damping mount 180 is revealed in FIGS. 7 and 8. Note from the latter figure, that the mount is coupled between the outer surface of the wall 152 of mounting component 150 and the inner surface 176 of outer wall 54. FIGS. 5–7 reveal a positioning component 182 adhesively attached to the forward wall 154 of mounting component 150 and shown to be in abutting engagement with the inside surface of forward wall 148. Component 182 functions during assembly to appropriately position the mounting component 150 to provide registry between its associated crystal detector 198 and the window 56. Attachment of the rearward vibration damping mount 178 and forward vibration damping mount 180 as well as component 182 is by an epoxy adhesive. Mounts 178 and 180 as well as component 182 are formed of an electrically insulative closed cell polymeric foamaceous material, for example as marketed by Darice, Inc. of Strongsville, Ohio. Thus mounted, vibration phenomena asserted at the outer wall 54 will be damped by the mounts 178 and 180. The amount of displacement thus will be minimized. Additionally, because of the span or bridging distance between those two mounts, displacement again is minimized to avoid noise phenomena due to the piezoelectric nature of the cadmium-telluride crystal detector. However, such motion will have no effect in producing noise generated by a variance of capacitance between components.

Rigidly mounted within mount cavity 156 is an elongate rectangular rigid crystal support 190. The electrically insulative support 190 is formed of a rigid material such as alumina and is provided having a thickness both assuring such rigidity and minimizing capacitance values between its outward and inward surfaces. The support 190 is seen to extend between oppositely disposed parallel edges 192 and 194 and to have a length substantially commensurate with the tip region 52. Rigid support 190 is configured as a printed circuit board which additionally supports the elongate rectangular cadmium-telluride crystal detector 196. Note that the oppositely disposed elongate sides or edges 198 and 200 of the crystal detector 198 (FIGS. 6 and 9) are spaced slightly inward from the corresponding edges 192 and 194 of crystal support 190. FIG. 5 reveals that the upper outwardly disposed face 202 is positioned closely adjacent the mount periphery 160. Correspondingly, the inwardly disposed face of the crystal detector 196 is compressibly abuttably positioned upon the outwardly disposed surface of crystal support 190. This association is rigid without the availability of mechanical movement and no intervening material is present except for a gold-covered biasing pad (not shown) having dimensions substantially commensurate with the surface of the inward face 204. This biasing pad is a portion of the printed circuit formed upon the crystal support 190, thus there is no occasion for movement of electrical leads. A gold coating is provided for this biasing pad, inasmuch as cadmium-telluride crystals conventionally are coated with an extremely thin layer of gold, the thickness of which is measurable in angstrom units. By providing a "gold on gold" compressive union, noise occasioned by triboelectric effects are avoided. Mounted upon the crystal support 190 and forming part of its printed circuit is a preamplifier or treatment circuit represented generally at 206. The components of this preamplifier circuit 206 are of the surface mount variety such that no potential for mechanical movement thereof is present. In the circuit, the forward or charge accumulating stage represented generally at 207 is positioned close to the biasing pad and associated crystal detector 196. As noted above, the components of this initial stage, typically comprising a bias resistor, a field effect transistor (JFET), a coupling capacitor and a feedback capacitor are the most sensitive components of the circuit 206 and will substantially amplify any noise signals generated in its environment. Crystal detector 196 is retained in compressive, freely abutting engagement with the biasing pad formed upon crystal support 190 by a retainer and grounding assembly represented generally at 208. As seen in FIGS. 7–9, the retainer assembly 208 is formed of a rigid polymeric material and is configured having a U or channel shape with integrally formed side portions 210 and 212 extending to respective inwardly depending dog structures shown respectively at 214 and 216 (FIGS. 7–9). The term "dog structures" is intended to mean any resiliently engaging retainer. The outward portion or top of the assembly 208 at 218 functions as a compression component. In this regard, it is formed having a very slight inward concave bow profile. The interior surface of the assembly 208 is coated with an electrically conductive metal, the outer surface of which is gold. When positioned over the crystal detector 196, the side portions 210 and 212 extend outwardly from the oppositely disposed sides 198 and 200 of detector 196, and the dog structures 214 and 216 engage the inward surface 220 (FIGS. 5, 7–9) of the crystal support 190. In this regard, the region of that surface adjacent the edges 192 and 194 is formed, again, as a portion of the printed circuit supported by support 190 and, as before, those edge surfaces are gold-coated and coupled to instrument or system ground such that ground is conveyed to the outwardly disposed face 202 of crystal detectors 196. In a preferred arrangement, the entire surface 220 is plated with an electrically conductive metal to provide a ground plane. Ground from that grounding component is specifically conveyed to the metal mounting component 150. This connection is represented in FIGS. 5 and 8 by an electrical lead 222. Note in connection with FIGS. 5 and 6 that the retainer and grounding assembly 208 extends to a rearward edge 224 which extends over the highly sensitive initial or charged accumulating stage 207 of the preamplifier circuit. Inasmuch as the interior surface of the assembly 208 is gold-coated and at ground potential, it thus forms an electrostatic shield over that sensitive stage. The rigid assemblage of crystal support 190 and the retainer and grounding assembly 208 is rigidly mounted upon the ledges 158 and 159 (FIGS. 8 and 9) with an epoxy adhesive. FIGS. 5 and 6 show that the output of the preamplifier circuit 206, as well as inputs thereto, from the console 12, occur as four leads represented generally at 226 which are coupled to a four lead conductor 228 extending to connection with the flexible cable 22 (FIG. 1). While the conductor 228 is supported within the accessing tube 50, its relative motion may occur with respect to accessing tube 50, as it will have no noise evoking consequences.

With the arrangement shown, no opportunity for capacitance variance is present in connection with the circuit components. In this regard, the confrontation of the inward surface 220 of crystal support 190 and the confronting surfaces of mount 150 as a bottom surface 162 is a ground-to-ground relationship. Thus, no electric field can be generated. Similarly, the grounded upper surface of the crystal detector 196 confronts a grounded aluminum foil 164 which, in turn, confronts a grounded window 56. Thus, any relative movement occasioned thereat will always represent a ground-to-ground relationship. The grounded cover 166 as well as the extended portion of the retainer grounding assembly 208 provides a rigid, grounded surface over the surface mounted components of the preamplification circuit 206. Thus, no mechanical motion is present, and no capacitance variation induced noise can be generated. The grounded cover 164 confronts the grounded inside surface 176 of the instrument tip region 52. Here, again, a ground-to-ground confrontational relationship exists such that no electric field is generated even though there may be relative movement between these components.

Figure 10:
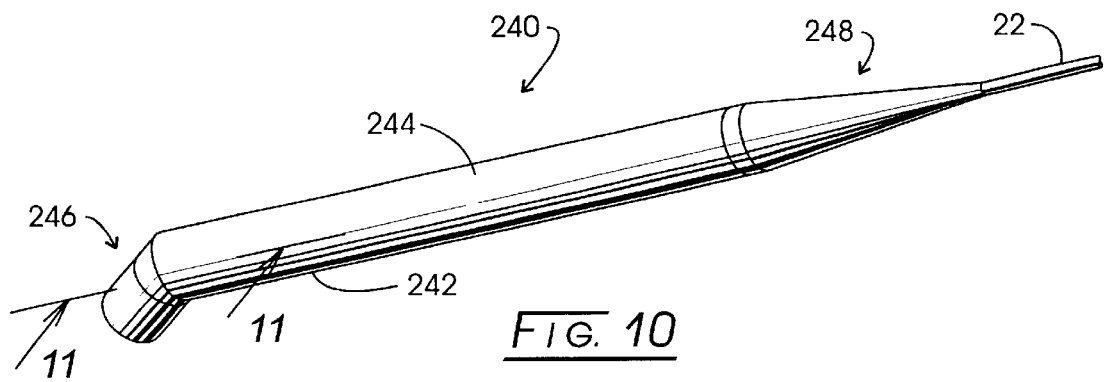
FIG. 10 is a pictorial representation of another probe apparatus embodiment of the invention.

The salient aspects of the invention as described in conjunction with FIGS. 2 and 4 also may be applied to hand-held probes utilized in the normal course of RIGS surgical procedures. A probe of a different geometric configuration is employed for that purpose. Referring to FIG. 10, such a probe instrument is represented generally at 240. The instrument 240 includes a housing 242 with a hand grippable region 244, a tip region 246 and a rearward region 248. Flexible cable 22 is connected with the instrument 240 at that rearward region 248.

Figure 11:
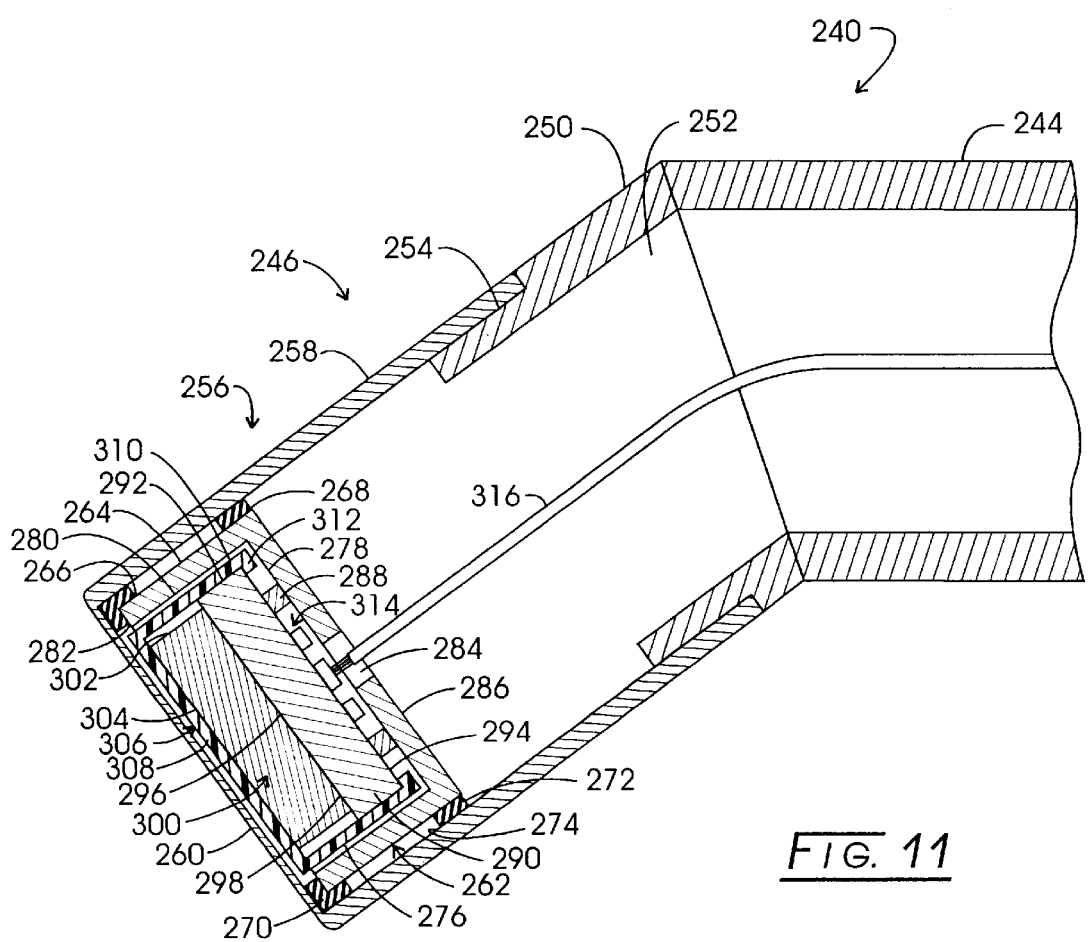
FIG. 11 is a partial sectional view taken through the plane 11—11 in FIG. 10.
Figure 12:
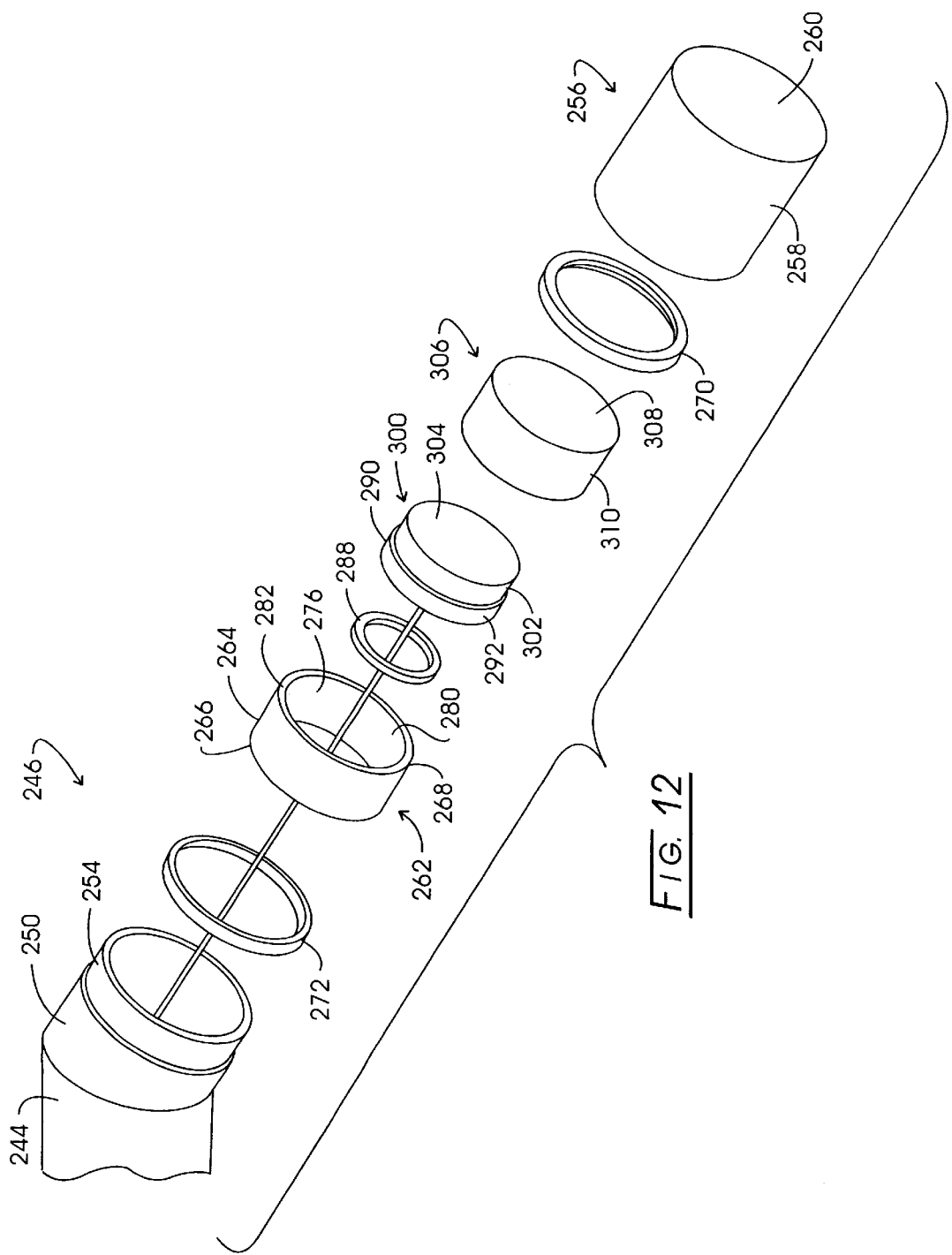
FIG. 12 is an exploded view of the tip region of the probe apparatus of FIGS. 10 and 11.

Looking to FIGS. 11 and 12, the tip region of instrument 240 is seen to include a cylindrical forward housing component 250 which is fixed to the hand-grip region 244 and provides about a 30° cant with respect to the axis of grip region 244. The sidewalls of the component 250 establish the rearward portion of a tip region cavity represented at 252 and the forward edge of that wall is machined to provide an annular flange or collar 254. Preferably, the components 244 and 250 are formed of a surgical grade stainless steel and are coupled to system or instrument ground at the rearward region 248. Connected to and extending from the collar 254 is a cup-shaped window assembly represented generally at 256. Connection of the assembly 256 at collar 254 may, for example, be provided with a surgical grade electrically conductive epoxy adhesive. The assembly 256 preferably is formed of aluminum, having a relatively cylindrical sidewall 258 which is integrally formed with a thin flat radiation transmissive window 260. Window assembly 256 also may be configured having an interiorly disposed cylindrical reinforcing component swaged thereto. Such a reinforcing component may be formed, for example, of tungsten so as to provide additional side shielding against the impingement of radiation. Positioned within the tip region cavity 252 is a cylindrical mounting component represented generally at 262. Component 262 is formed of electrically conductive material which further functions to attenuate radiation, being formed, for example, of tungsten or lead. Finite support portions at the cylindrical outer surface 264 as at 266 and 268 are spaced apart a span or bridging distance and are attached to respective outer and inner vibration damping mounts 270 and 272. These mounts, as before, are formed of a closed cell polymeric foam material and are adhesively coupled between the inner cylindrical surface 274 of cup-shaped window assembly 256 and the support portions 266 and 268. Connection is by an epoxy adhesive. Such damping mounting, while permitting a minor amount of movement, functions to protect the cadimium-telluride crystal detector supported by the mount 262 from the noise phenomena generated by its inherit piezoelectric characteristics. Formed within the mount 262 is a mount cavity 276 which is cylindrically-shaped and extends from a bottom surface 278 of circular periphery to define a cylindrical side surface 280 extending to an outwardly disposed peripheral edge 282 of annular configuration. It may be noted that the outer vibration damping mount 270 is configured as a shortened cup, the forwardly disposed component of which rests against the peripheral edge 282. A cylindrical passageway or opening 284 extends from the rearward surface thereof at 286 to bottom surface 278. Mounted upon or integrally formed with the bottom surface 278 is an annular ring-shaped standoff 288. Formed of the same metal material as the mount 262, the standoff 288 is electrically conductive and, implemented as a separate component, is attached to the bottom surface 278 in a manner providing for the transfer of ground potential to the mount 262. Rigidly connected to the forward surface of standoff 288 is a rigid crystal support 290, the cylindrical side surface 292 of which is spaced from sidewall 280 of the mounting component 262. Formed of a rigid electrically insulative material such as alumina, crystal support 290 also is configured to support a printed circuit. In this regard, its inward surface 294 is configured to support preamplifier circuit components. It will support at least the noted first stage or charge collecting stage of such a preamplifier circuit. The components of the preamplifier circuit which are mounted in circuit board fashion upon the surface 294 are surface mounted to assure their rigidity against mechanical motion. The printed circuit carried by the crystal support 290 extends through its thickness to a forwardly disposed gold coated bias pad (not shown) formed upon its forward surface 296. Compressively but freely abuttably positioned upon that forward surface 296 and associated bias pad is the inward surface 298 of a cadmium-telluride crystal 300. Note that the cylindrical side surface 302 of the crystal detector 300 is spaced inwardly from the cylindrical side surface 280 of mount cavity 276. The forward face 304 of the crystal detector 300 is positioned adjacent the peripheral edge 282 of the mount cavity 276.

As in the earlier embodiment, the crystal detector 300 is compressively retained in position upon the bias pad supporting crystal mount surface 296 by a cup-shaped retainer and grounding assembly represented generally at 306. Assembly 306 is formed of a resilient polymeric material which is electrically insulative. However, as before, the inside surface thereof is coated with a very thin gold layer. In this regard, the layer is selected to convey ground potential but not to attenuate any significant component of impinging radiation. Assembly 306 includes a forward annular compression component 308 which is integrally formed with a cylindrical side portion 310 (FIG. 12). Side portion 310 extends to an inwardly depending annular dog structure 312. Structure 312 engages the outer periphery of crystal support inward surface 294 and inside portion, 310, being in tension, urges the compression component 308 into compressive engagement with the forward face 304 of crystal detector 300. To enhance this compressive engagement, the component 308 may be concavely bowed inwardly a slight amount. Note that the side portion 310 of the assembly 306 is spaced slightly outwardly from the side surface 302 of crystal 300. Also, the forward surface of compression component 308 is seen to be spaced slightly inwardly from the inside surface of window 260. This gap so formed functions in the nature of an acoustic filter with respect to the forward face 304 of the crystal detector 300.

Outputs and inputs to the preamplifier circuit, certain components of which are seen at 314, are by a four lead cable 316, and cable 316 also supplies bias and circuit power to the treatment circuit. As before, inasmuch as the cable is carrying treated and amplified signals, a small amount of motion and part of thereto will have no noise generating consequence. With the system or instrument ground supplied from the cable 316 to the preamplifier circuit is extended in printed circuit fashion both to the standoff 288 and to the outer periphery of crystal support inward surface 294. This grounding component of the printed circuit is coated with gold to avoid triboelectric effects and is transmitted by virtue of the gold coating upon the inner surface of retainer assembly 306 to the crystal forward face. Additionally, that ground is supplied through the standoff 288 to the metal mounting component 262. As before, the printed circuit components are rigidly secure and confront a grounded surface 278 such that no variation in a capacitive confrontation is made available. Similarly, the biasing pad at the forward surface 296 of crystal support 290 does not move nor does the crystal detector 300 which is freely abuttably compressibly positioned against it. Thus, while minor damped movement may occur in conjunction with the mounting component 262, such movement will not be the occasion of noise generation due to the varying capacitive condition. Note, additionally, that the cup-shaped window assembly 256, by virtue of its connection with the housing component 250 is grounded. Similarly, mounting component 262 is grounded, and thus, a ground-to-ground condition exists such that no electric field is present between these components and no noise generation is occasioned by their relative movement.

Figure 13:
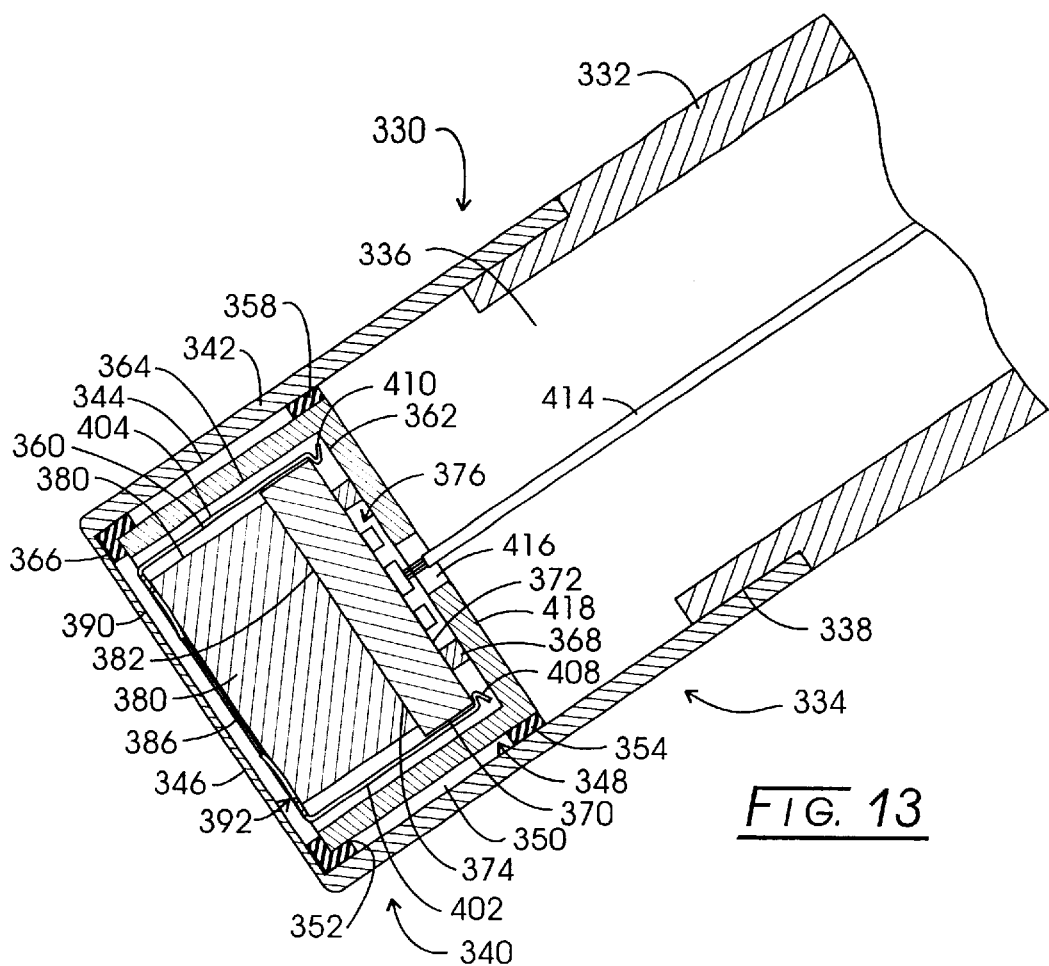
FIG. 13 is a partial sectional view of another probe apparatus embodiment of the invention.

A variation of the probe instrument 240 is depicted in FIG. 13. Looking to that figure, the forward component of a probe instrument is represented in general at 330. Probe 330 is structured for the purpose of carrying out sentinel lymph node detection. As such, its tubular metal housing with wall 332 is not canted at the tip region 334. However, the wall 332 does provide a tip region cavity the rearward portion of which is seen at 336. An annular collar 338 is machined into the forward portion of wall 332 for the purpose of accepting and supporting a cup-shaped window assembly represented generally at 340. As before, the assembly 340 is formed of aluminum, having a relatively thicker sidewall 342 with an interior cylindrical surface 344. A thin window 346 is formed integrally with the sidewalls 342.

Positioned within the tip region cavity 336 is a mounting component represented generally at 348. Component 348 is configured to attenuate radiation, and for the instant embodiment, the radiation will be of relatively higher gamma energy as is derived with the radionuclide $^{99m}$Tc. In this regard, the component will be fashioned of tungsten or lead. As before, the mounting component is formed with a cylindrical outer surface 350. Located upon this surface 350 are outward and inward finite support portions shown respectively at 352 and 354. If mounted intermediate the interior surface 344 of sidewall 342 and the outward support portion 352 is an outward vibration damping mount 356 configured substantially similarly to that mount 270 and formed of the same material. An inward vibration damping mount 358 is positioned intermediate the interior surface 344 and finite inward support portion 354. Mount 358 is configured substantially similarly to mount 272 discussed above.

Formed within the mounting component 348 is a cylindrical mount cavity 360 having a bottom surface 362, and cylindrical sidewall 364 extending to an annular peripheral edge 366. Mounted upon or formed integrally with the bottom surface 362 of mount cavity 360 is an annular or ring-shaped standoff 368 which, as before, preferably is formed of the same material as the mounting component 348. The connection required, however, is one for the conveyance of ground potential to the component 348. Rigidly fixed to the forward surface of standoff 368 is a rigid crystal support 370 having an inward surface 372 and an outward surface 374. The support 370 is formed of a rigid, electrically insulative material, such as alumina, and is configured having a thickness to minimize capacitance between its inward surface and outward surface. The support 370 is configured to contain a printed circuit which will include, at least, the charge accumulating initial stage of a preamplifier and, for the instant embodiment, an entire preamplifier circuit incorporating surface mounted components, certain of which are seen at 376 extending inwardly from the inward surface 372. As before, this printed circuit configuration continues through the support 370 to provide a biasing pad (not shown) upon its outward surface 374 having a dimension substantially commensurate with a cadmium-telluride crystal detector shown at 380. In this regard, the inward face 382 of crystal 380 is freeably abuttably but compressibly engaged with that biasing pad at the outward surface 374. The biasing pad is gold-coated or formed of gold in consonance with the very thin gold coating at the crystal face 382 to avoid triboelectric phenomena. It may be observed that the cylindrical sidewall 384 of crystal detector 380 is spaced from the mount cavity sidewall 364 to define a side gap and shows a crystal thickness enlarged over the earlier described embodiments. This thickness along with selected bias values provides for operating the crystal in a trapping dependent mode wherein essentially all carriers, evoked in consequence of a photon event, are trapped. The forward face 386 of crystal 380 is seen to be located essentially coplanar with the peripheral edge 366 of the mount cavity 360.

Figure 14:
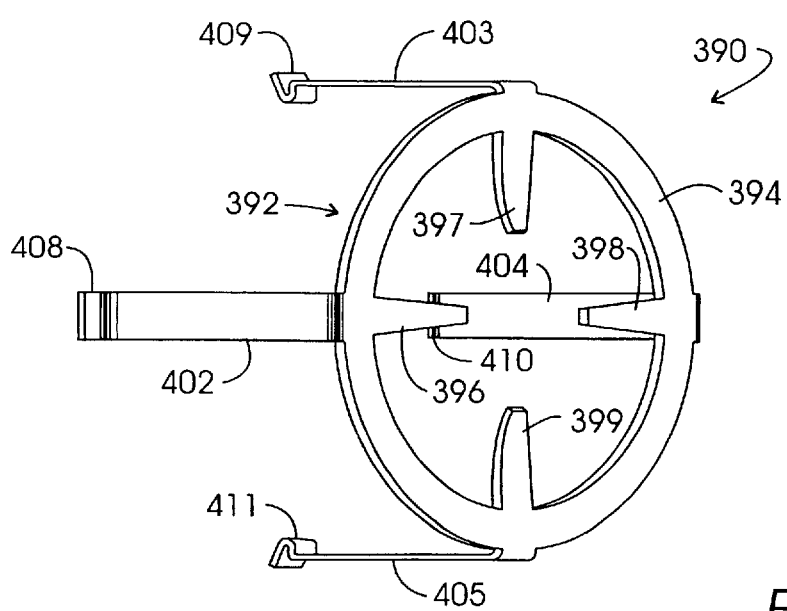
FIG. 14 is a pictorial representation of a retainer and grounding assembly utilized with the probe apparatus embodiment of FIG. 13.

Looking additionally to FIG. 14, a retainer and grounding assembly represented generally at 390 retains the crystal detector 380 in compressive, freely abutting engagement with the bias pad at the crystal support outward surface 374. Assembly 390 is formed of a gold-plated spring-like or resilient metal such as beryllium copper. Its compression component is represented generally at 392 and includes a flat ring portion 394 having inwardly depending thin tines which engage the crystal forward face 386, asserting ground thereat as well as a compressive retaining force. Integrally formed side legs 402–405 extend to respective dog structures 408–411. Seen in FIG. 13, the dog structures 408–411 engage the inward surface 372 of crystal support 370 at its periphery. At that periphery, as before, there is provided a gold-plated gold ground surface as part of the preamplifier printed circuit. The inputs and outputs to that preamplifier printed circuit are coupled with a four strand lead 414 which extends through a passageway or opening 416 extending between the back surface 418 of mounting component 348 and the mount cavity bottom surface 362. As before, relevant movement of this cable 414 which is coupled to flexible cable 22 (FIG. 1) is of no consequence with respect to noise generation. With the arrangement shown, there is no relative movement between the charge carrying or bias-based elements of the instruments and a confronting surface. Thus, there is no variable capacitance induced noise. Similarly, inasmuch as the cup-shaped window assembly 340 is grounded and the mounting component 348 is grounded, relevant movement therebetween is of no consequence with respect to noise generation.

Figure 15A:
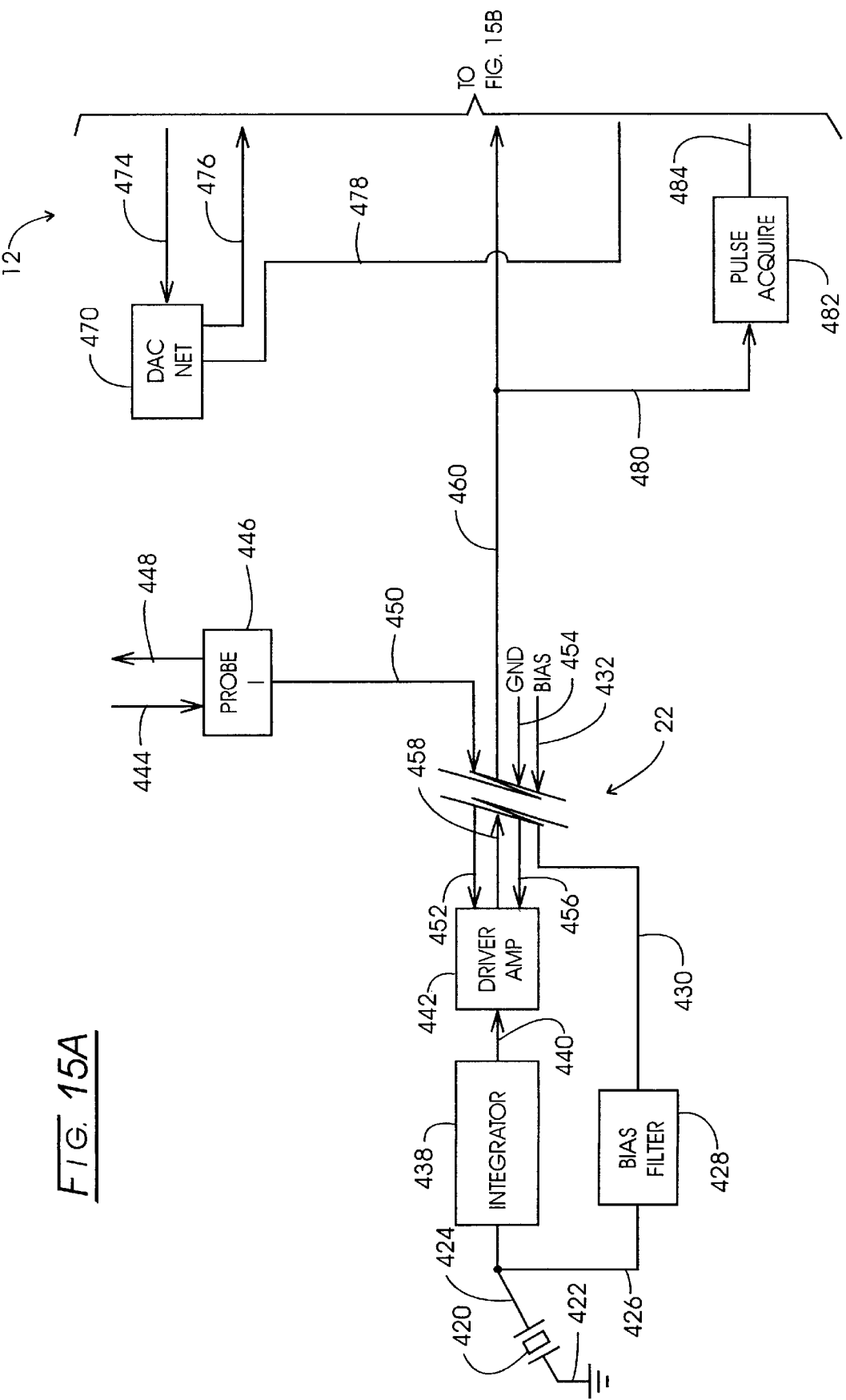
FIGS. 15A and 15B combine as labeled thereon to provide a block diagramatic representation of the circuits employed with the control assembly and probe apparatus shown in FIG. 1.
Figure 15B:
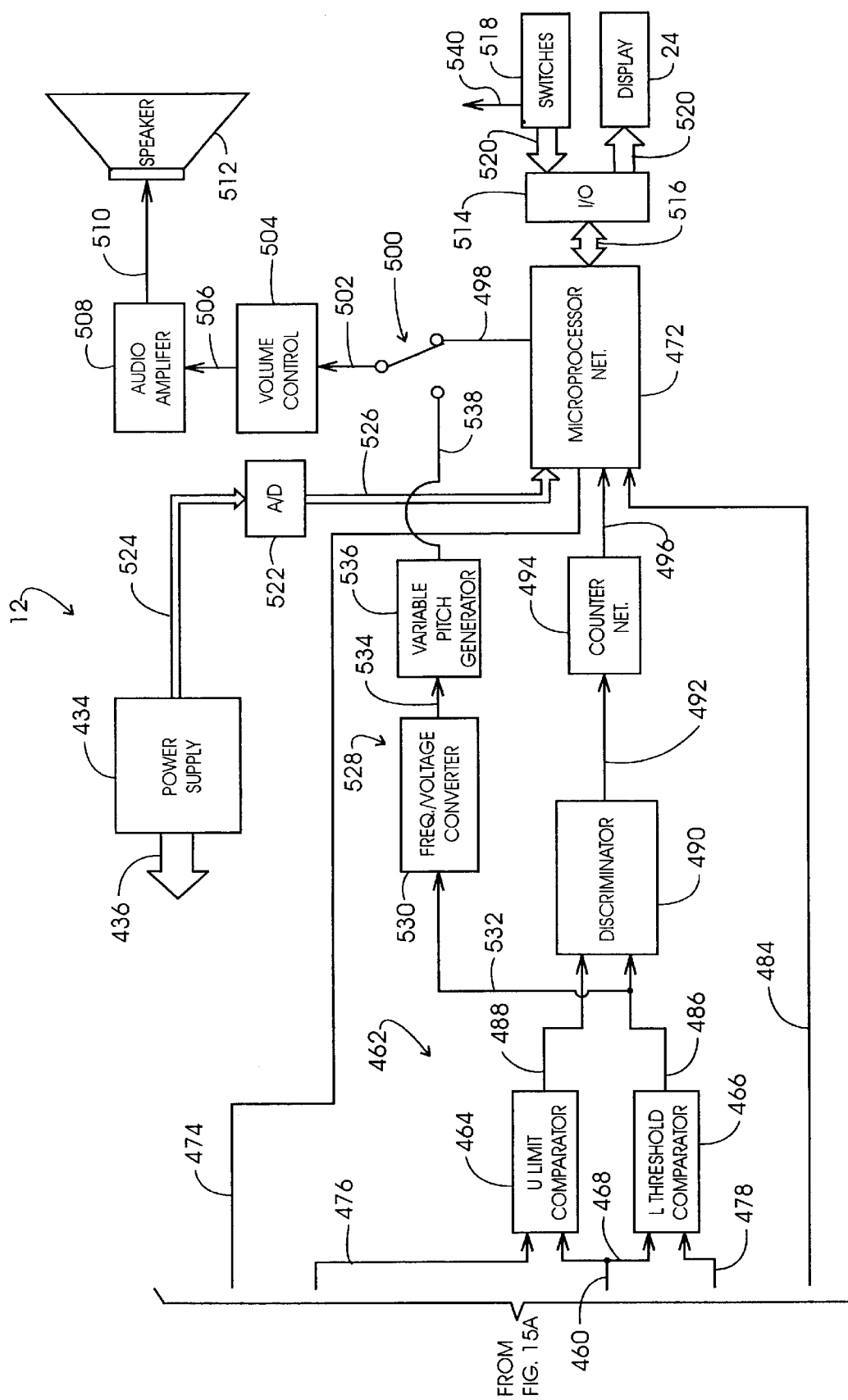

Referring to FIGS. 15A and 15B, a block diagrammatic representation of the circuitry employed with the system 10 is provided. These figures should be considered in mutual adjacency in the manner labeled thereon. In FIG. 15A, a cadimium-telluride crystal detector is represented at 420. Detector 420 is shown having its forward face coupled to ground as represented by a line 422. For the embodiments above described, this line is representative of the retainer and grounding assemblies. The opposite face of the crystal 420 is shown as having a positive bias applied thereto from a line 424. Line 424 is representative of the gold-coated bias pads supported by the rigid crystal supports. Line 424 is seen coupled via a line 426 to a bias filter represented at block 428. The input to filter 428 is represented at line 430 as being applied through the cable described earlier at 22. Cable 22 also is represented generally in the instant figure. The bias input as represented at line 432, emanates from a multi-output power supply shown in FIG. 15B at block 434. These various outputs of the power supply 434 are represented, in general, by an arrow 436 extending from block 434.

Returning to FIG. 15A, line 424 extending from the crystal detector 420, carrying a count-related charge output corresponding to radiation emissions impinging upon crystal 420, is seen to extend to an integrator stage represented at block 438. This integrator stage 438 forms part of the highly sensitive initial or charge collection stage of a preamplification function which, described above, is also mounted upon a rigid alumina crystal support. The integrated valuation of detected radiation then is shown directed, as represented by line 440, to a driver amplification network shown at block 442. One such preamplification circuit, comprised of blocks 438 and 442, is described in U.S. Pat. No. 5,441,050 by Thurston and Olson issued Aug. 15, 1995, entitled, "Radiation Responsive Surgical Instrument." A d.c. power supply is provided from the power supply, represented at block 434 and arrow 436 (FIG. 15B), for the preamplification function. This power supply is directed, as represented at line 444, to a probe network represented at block 446. Under microcomputer control, as represented at line 448, the network 446 develops signals, for example, determining whether the probe instrument 14 has been properly connected to the console 12. Delivery of the d.c. power supply for the preamplification function is represented at lines 450 and 452. Line 452 forms a component of flexible cable 22. System or instrument ground is provided from the power supply, as represented at block 434, is provided at line 454 and line 456 which forms a component of cable 22.

The preamplification circuit forms part of a signal treatment function which ultimately develops count signals. In this regard, the output of the preamplification circuit at line 458 is conveyed via cable 22 for introduction to the control of system 12, the corresponding signal carrying line of which is represented at line 460. Line 460 extends to the input of an energy window network represented in FIG. 15B, in general, at 462. Network 462 functions to evaluate the count-based outputs at line 460 in terms of gamma energy levels of interest, to derive validated photon count signals. It may be observed that the energy window network 462 includes an upper limit comparator represented at block 464, as well as a lower threshold comparator represented at block 466. The count output signal, which will include varieties of noise, including Compton scattering based phenomena for the high energy mode of operation, are submitted simultaneously to each of these comparator functions 464 and 466 as represented at lines 468 and 460. Correspondingly, the comparison values or limits associated with the upper limit comparator 464 are applied from a digital-to-analog converter (DAC) as seen in FIG. 15A at block 470. Converter 470 is under the control of a microprocessor network represented at block 472 (FIG. 15B), such digital control to device 470 being asserted as represented at line 474. Thus, the upper limit value asserted at comparator 464 is provided at line 476 from DAC 470. Correspondingly, the lower threshold value for comparator function 466 is asserted from DAC 470 via line 478. FIG. 15A also reveals that signals at line 460 are directed, as represented at line 480, to a pulse acquire function represented at block 482. Network 482 functions, when activated by the microprocessor function 472, to acquire the value of the highest pulse amplitude witnessed at line 460. Periodically, this information is transmitted to the microprocessor network 472 as represented at line 484. Representing a form of peak detector, the network 482 sometimes is referred to as a "snapshot circuit."

With appropriate operation of the semiconductor crystal 420, it is possible to observe a distinct voltage output pulse from the preamplifier or forward signal treatment components for each interacting radiation quantum (photon or fast particle) that deposits a significant amount of energy in the crystal detector 420 volume. Under such circumstances, the amplitude of the output pulse reflects the induced charge from the detector which is often an indicator of the initial energy of the individual quantum. The incoming signals, additionally, may represent spurious phenomena, such as cosmic rays and the like, and for sentinel node identification applications, the incoming signals also typically will include a Compton scattering form of noise. Accordingly, the energies of the incoming signals are evaluated at the energy window network 462 as seen in FIG. 15B. The lower threshold comparator function 466 will promulgate a pulse at line 486 when the signal asserted thereat exhibits an amplitude of value equal to or above a threshold value established, as noted above, from line 478. Correspondingly, the signals at line 468 will be evaluated by the upper limit comparator function 464 such that when the incoming signal exhibits an amplitude of value above the upper limit value established from line 476, a pulse will be promulgated at line 488. For the RIGS component of the system 10, outputs from lines 486 and 488 then are directed to the input of an asynchronous, sequential, fundamental mode discriminator circuit represented at block 490. Circuits, as at block 490, while being sequential in nature, are not synchronized in any way with a clock signal. Such circuits as at block 490, are described in U.S. Pat. No. 5,475,219 by Olson, entitled "Validation Of Photon Emission-Based Signals Using An Energy Window Network In Conjunction With A Fundamental Mode Discriminator Circuit," issued Dec. 12, 1995. The discriminator function represented at block 490 serves to generate count signals in the form of finite pulses at line 492. Such pulses occur in the presence of the signal at line 460 which represents a photon emission which is valid from the standpoint of the gamma energy range of interest associated with it.

The pulsed signals at line 492 are provided to a counter network represented at block 494. These pulses at line 492 are counted by network 494, whereupon, as represented at line 496, count data is submitted to the microprocessor network 472 for statistical analysis. The function of counter network 494 may be implemented in software as described in the above referenced U.S. Pat. No. 4,889,991. Microprocessor network 472 performs under a variety of operational modes, depending upon the user inputs to the function switches at array 28 as well as to a calibration input. In general, it functions to provide outputs to two output components, one aural type generated from a speaker, and the other a visual output at display 44. Generally, a "siren" type of signal manifested with a predetermined frequency variation is asserted as represented by line 498 through a mode switch represented at 500 and line 502 to a volume control function represented at block 504. The volume adjusted signal is directed, as represented at line 506, to an audio amplification circuit represented at block 508. The circuit at block 508, in turn, is represented at line 510, which drives a speaker 512. With the noted "siren" arrangement, the frequency output from speaker 512 increases with an exponential change from 20 Hz to 1200 Hz when the average count rate determined by system 10 exceeds a preset threshold level which is statistically significant over background count rates. The "siren" mode is accessed by the user from console 12 by sequentially actuating switch 36 then switch 34 (FIG. 1). This "siren" mode of performance is described in detail in the above-referenced U.S. Pat. No. 4,889,991 by Ramsey and Thurston.

Microprocessor network 472 performs in conventional fashion with an input/output network as represented at block 514 and dual directional arrow 516. This input/output port function 514 provides for appropriate scanning of pertinent console 12 mounted switches as represented at block 518 and arrow 520. The output port also drives the display 24, again identified by the same numeration but shown in block form, as represented by arrow 520. Further, microprocessor network 472 may be employed to monitor the performance of the power supply represented at block 434. This is shown as being carried out by the interaction of the microprocessor network 472 with an analog-to-digital converter represented at block 522 and having an association represented by arrows 524 and 526. The converter 522 functions to digitize analog values at the power supply 434 for submittal to the microprocessor network 472.

Components of the lymph node mapping or high gamma energy aspects of system 10 are provided as an adjunct circuit represented in general at 528. The components of this adjunct system 528 include a frequency-to-voltage converter represented at block 530 which responds to the count-associated signals from the lower threshold comparator at block 466 as represented by lines 486 and 532 to provide a rate level signal corresponding with the frequency of those count-associated signals at line 486. This signal will be provided as a d.c. voltage level which extends within a dynamic range of, for example, 0 to 2.5 Volts. That signal then is directed to a variable pitch generator function represented at block 536. The function at block 536 serves to provide the noted initial ranging feature and a count rate thresholding feature which may be controlled from knob 48 or the up/down switches 42 and 40 (FIG. 1). Additionally included in the function 536 is a post thresholding amplification network having a gain corresponding with the threshold level value to permit full scale performance of the speaker 512 and linear LED array 44 (FIG. 1). The output of function 536 is shown at line 538 extending to one terminal of mode switch 500. Microprocessor network 472 continues to provide volume control during the operation of generator function 536 in response to actuation of switch 38 (FIG. 1). An output represented at arrow 540 extends to a "beep" generator (not shown) which provides an auxiliary audible switch feedback for the user.

Since certain changes may be made to the above described system and apparatus without departing from the scope of the invention herein involved, it is intended that all matter contained in the description thereof and shown in the accompanying drawings shall be interpreted as illustrative and not in a limiting sense.

What is claimed is:

1. An instrument for detecting and locating sources of radiation emission, comprising:

a housing assembly extending from a hand grippable region to a tip region, said tip region having a substantially flat radiation transmissive window and an internal surface defining a tip region cavity;

a mounting component within said tip region cavity, formed of material attenuating said radiation, extending between first and second finite support portions mutually spaced apart a span distance, having side portions defining a mount cavity with an outwardly disposed peripheral edge in spaced adjacency with said window;

a rigid crystal support formed of electrically insulative material and rigidly mounted within said mount cavity;

a crystal detector having an outwardly disposed face adjacent to said mount peripheral edge confronting said window and an opposite, inwardly disposed face positioned upon said crystal support and responsive to radiation passing through said window to provide a detector output;

a bias conveying and signal receiving circuit in electrical communication with said crystal detector inwardly disposed face;

a retainer and grounding assembly having an electrical grounding surface in abutting, compressive engagement with said crystal detector outwardly disposed face;

a first vibration damping mount supporting said mounting component at said first finite support portion in spaced relationship from said tip region internal surface; and a second vibration damping mount supporting said mounting component at said second finite support portion in spaced relationship from said tip region internal surface; and said mounting component being supported as an open span along said span distance between said first and second vibration damping mounts.

2. The instrument of claim 1 in which:

said crystal detector is mounted upon said crystal support to position its said outwardly disposed face in close parallel planar relationship with said entrance portion outwardly disposed peripheral edge; and said mounting component is configured to position said crystal detector outwardly disposed face in closely spaced relationship with said tip region flat window.

3. The instrument of claim 1 in which:

said housing assembly tip region is configured to provide an electrically grounded shield surmounting said mounting component; and said mounting component is formed of an electrically conductive material and is connected with electrical ground.

4. The instrument of claim 1 in which said first and second vibration damping mounts are formed of a closed cell polymeric foamaceous material.

5. An instrument for detecting and locating sources of radiation emission, comprising:

a housing assembly extending from a hand grippable region to a tip region, said tip region having a substantially flat radiation transmissive window and an internal surface defining a tip region cavity;

a mounting component within said tip region cavity, formed of material attenuating said radiation, extending between first and second finite support portions mutually spaced apart a span distance, having side portions defining a mount cavity with an outwardly disposed peripheral edge in spaced adjacency with said window;

a rigid crystal support formed of electrically insulative material and rigidly mounted within said mount cavity;

a crystal detector having an outwardly disposed face adjacent to said mount peripheral edge confronting said window and an opposite, inwardly disposed face positioned upon said crystal support and responsive to radiation passing through said window to provide a detector output;

a bias conveying and signal receiving circuit in electrical communication with said crystal detector inwardly disposed face;

a retainer and grounding assembly having an electrical grounding surface in abutting, compressive engagement with said crystal detector outwardly disposed face, said retainer and grounding assembly comprising a resilient, inwardly biased compression component having an inward surface positioned in compressing relationship over said crystal detector outwardly disposed face and having an integrally formed side portion extending to a dog structure engaging said crystal support to derive said compressing relationship;

a first vibration damping mount supporting said mounting component at said first finite support portion in spaced relationship from said tip region internal surface; and a second vibration damping mount supporting said mounting component at said second finite support portion in spaced relationship from said tip region internal surface; and said mounting component being supported as an open span along said span distance between said first and second vibration damping mounts.

6. The instrument of claim 5 in which said retainer and grounding assembly electrical grounding surface comprises a thin, metal surface supported upon said compression component inward surface.

7. The instrument of claim 5 in which:

said crystal support includes an outward support surface and an oppositely disposed inward surface;

said crystal detector inwardly disposed face is mounted in abutting relationship upon said crystal support outward support surface; and said bias conveying and signal receiving circuit includes a metal biasing surface formed upon said crystal support outward support surface and in compressing abutting contact with said crystal detector inwardly disposed face.

8. The instrument of claim 7 including:

a treatment circuit mounted upon said crystal support and in electrical communication with said metal biasing surface for electrically treating said detector output to provide output signals corresponding therewith.

9. The instrument of claim 8 in which said metal biasing surface and said treatment circuit comprise a printed circuit including a preamplifier network deriving said output signals.

10. The instrument of claim 7 in which:

said crystal support inward surface extends to a peripheral edge;

including an electrically grounded metal surface formed upon said crystal support inward surface adjacent said peripheral edge; and said retainer and grounding assembly electrical grounding surface extends to said dog structure; and said dog structure is abuttably, electrically engaged with said grounded metal surface at said inward surface peripheral edge.

11. The instrument of claim 7 including:

a treatment circuit including a preamplifier network configured with a printed circuit mounted upon said crystal support inward surface and in electrical communication with said metal biasing surface for electrically treating said detector output to provide output signals corresponding therewith.

12. Probe apparatus for detecting and locating sources of radiation emission, comprising:

a housing assembly extending from a hand grippable region to a tip region, said tip region having a substantially flat radiation transmission window and an internal surface defining a tip region cavity;

a mounting component formed of material attenuating said radiation mounted within said tip region cavity, having side portions defining a mount cavity with an outwardly disposed peripheral edge in spaced adjacency with said window;

a rigid crystal support formed of electrically insulative material, having an outward surface and an oppositely disposed inward surface, rigidly mounted within said mount cavity;

a crystal detector having an outwardly disposed face adjacent to said mount peripheral edge and an oppositely disposed inward surface abuttably positioned and rigidly supported upon said crystal support outward surface, and responsive to said radiation emission to provide a detector output;

a bias conveying and signal receiving circuit rigidly mounted upon said crystal support in bias conveying direct electrical communication with said crystal detector inwardly disposed face and having an electrical ground; and a retainer and grounding assembly including a resilient, inwardly biased compression component having an inward surface carrying an electrical grounding surface connected with said electrical ground positioned in compressive relationship over said crystal detector outwardly disposed face and having an integrally formed side portion extending to a dog structure engaging said crystal support inward surface to derive said compressive relationship.

13. The probe apparatus of claim 12 in which:

said housing assembly tip region is configured to provide an electrically grounded shield surmounting said mounting component; and said mounting component is formed of an electrically conductive material and is connected with electrical ground.

14. The probe apparatus of claim 12 in which said retainer and grounding assembly electrical grounding surface comprises a thin, metal surface supported upon said compression component inward surface.

15. The probe apparatus of claim 12 in which:

said bias conveying and signal receiving circuit includes a metal biasing surface formed upon said crystal support outward support surface and in compressive abutting contact with said crystal detector inwardly disposed face.

16. The probe apparatus of claim 14 in which said bias conveying and signal receiving circuit includes:

a treatment circuit mounted upon said crystal support and in electrical communication with said metal biasing surface for electrically treating said detector output to provide output signals corresponding therewith.

17. The probe apparatus of claim 16 in which said metal biasing surface and said treatment circuit comprise a printed circuit including at least one stage of a preamplifier network deriving said output signals.

18. Probe apparatus for locating source of radiation emission in tissue, comprising:

a hand grippable base portion;

an elongate accessing tube extending from said base portion to a tip region having a wall with an interior surface defining a side looking tip region cavity extending to a generally rectangular periphery, said tip region cavity being enclosed at said periphery by a radiation transmissive side looking window having an internally disposed window surface;

a mounting component, within said tip region cavity having side portions with an external mount surface extending between first and second support portions mutually spaced apart a mount distance, said side portions extending to a mount peripheral edge in spaced adjacency with said internally disposed window surface and defining a side opening mount cavity;

a rigid crystal support formed of electrically insulative material rigidly mounted within said mount cavity and having a crystal support surface extending between oppositely disposed side edges;

a crystal detector having an outwardly disposed face adjacent said mount peripheral edge and an opposite, inwardly disposed face abuttably positioned upon said crystal support surface and responsive to radiation passing through said window to provide a detector output;

a bias conveying and signal receiving circuit in electrical communication which said crystal detector inwardly disposed face;

a retainer and grounding assembly having an electrical grounding surface in abutting, compressive engagement with said crystal detector outwardly disposed face;

a first vibration damping mount positioned intermediate said tip region interior surface and said mounting component external mount surface at said first support portion;

a second vibration damping mount positioned intermediate said tip region interior surface and said mounting component external mount surface at said second support portion; and said mounting component being supported as an open mount along said span distance between said first and second vibration damping mounts.

19. The probe apparatus of claim 18 in which said first and second vibration damping mounts are formed of an electrically insulative foamaceous polymeric material.

20. The probe apparatus of claim 19 in which said polymeric material is a closed cell foamaceous material.

21. The probe apparatus of claim 19 in which:

said mounting component is formed of an electrically conductive material; and said mounting component and said tip region are coupled with electrical ground.

22. The probe apparatus of claim 18 in which:

said mounting component side portions are generally cylindrically shaped, formed of an electrically conductive material, and said peripheral edge is configured as a rectangle;

said crystal support is configured generally having sides defining an elongate rectangular periphery;

said bias conveying and signal receiving circuit includes a metal biasing-surface formed upon said crystal support surface and in compressive abutting contact with said crystal detector inwardly disposed face.

23. The probe apparatus of claim 22 including:

a treatment circuit mounted upon said crystal support and in electrical communication with said metal biasing surface for electronically treating said detector output to provide output signals corresponding therewith.

24. The probe apparatus of claim 23 in which said metal biasing surface and said treatment circuit comprise a printed circuit including a preamplifier network deriving said output signals.

25. Probe apparatus for locating source of radiation emission in tissue, comprising:

a hand grippable base portion;

an elongate accessing tube extending from said base portion to a tip region having a wall an interior surface defining a side looking up region cavity extending to a generally rectangular periphery, said tip region cavity being enclosed at said periphery by a radiation transmissive side looking window having an internally disposed window surface;

a mounting component, within said tip region cavity having side portions with an external mount surface extending between first and second support portions mutually spaced apart a mount distance, said side portions extending to a mount peripheral edge in spaced adjacency with said internally disposed window surface and defining a side opening mount cavity, said mounting component side portions being generally cylindrically shaped, formed of an electrically conductive material, and said peripheral edge is configured as a rectangle;

a rigid crystal support formed of electrically insulative material rigidly mounted within said mount cavity and having a crystal support surface extending between oppositely disposed side edges and configured generally having sides defining an elongate rectangular periphery;

a crystal detector having an outwardly disposed face adjacent said mount peripheral edge and an opposite, inwardly disposed face positioned upon said crystal support surface and responsive to radiation passing through said window to provide a detector output;

a bias conveying and signal receiving circuit in electrical communication which said crystal detector inwardly disposed face and including a metal biasing-surface formed upon said crystal support surface and in compressive abutting contact with said crystal detector inwardly disposed face;

a treatment circuit mounted upon said crystal support and in electrical communication with said metal biasing surface for electronically treating said detector output to provide output signals corresponding therewith;

a retainer and grounding assembly having an electrical grounding surface in abutting, compressive engagement with said crystal detector outwardly disposed face, said retainer and grounding assembly comprising a resilient, inwardly biased compression component having an electrically conductive, grounded inward surface positioned in compressing relationship over said crystal detector outwardly disposed face and having integrally formed side portions extending to a dog structure engaging said crystal support sides to derive said compressive relationship;

a first vibration damping mount positioned intermediate said tip region interior surface and said mounting component external mount surface at said first support portion;

a second vibration damping mount positioned intermediate said tip region interior surface and said mounting component external mount surface at said second support portion; and said mounting component being supported as an open span along said span distance between said first and second vibration damping mounts.

26. The probe apparatus of claim 25 in which:

said treatment circuit includes the initial charge accumulating stage of a preamplifier circuit; and said retainer and grounding assembly grounded inward surface extends over said initial charge accumulating stage.

27. The probe apparatus of claim 26 in which:

said crystal support includes an inward surface disposed opposite said crystal support surface;

including an electrically grounded metal surface formed upon said crystal support inward surface adjacent a said side;

said retainer and grounding assembly grounded inward surface extends to said dog structure; and said dog structure is abuttably, electrically engaged with said grounded metal surface adjacent a said side.

28. Probe apparatus for locating a source of radiation emission in tissue, comprising:

a hand grippable base portion;

an elongate accessing tube extending from said base portion to a tip region with an internal surface defining a side looking tip region cavity extending to a generally rectangular periphery, said tip region cavity being enclosed at said periphery by a radiation transmissive side-looking window having an internally disposed window surface;

a mounting component within said tip region cavity, having side portions defining a mount cavity, said side portions extending to a generally rectangular mount peripheral edge in spaced adjacency with said internally disposed window surface;

a rigid crystal support formed of electrically insulative material, rigidly mounted within said mount cavity, configured having an elongate generally rectangular periphery with oppositely disposed side edges at least coextensive with said mount cavity;

a crystal detector having an outwardly disposed face adjacent said mount peripheral edge and an opposite, inwardly disposed face rigidly positioned upon said crystal support surface, and responsive to radiation passing through said window to provide a detector output;

a bias conveying and signal receiving circuit rigidly mounted upon said crystal support in bias conveying direct electrical communication with said crystal detector inwardly disposed face and having an electrical ground; and a retainer and grounding assembly including a resilient, inwardly biased compression component with an inwardly disposed electrical grounding surface carrying said electrical ground positioned in abutting compressive relationship over said crystal detector outwardly disposed face and having integrally formed side portions extending to a dog structure engaging said crystal support oppositely disposed side edges to derive said compressive relationship.

29. The probe apparatus of claim 28 said retainer and grounding assembly electrical grounding surface comprises a thin, metal surface supported upon said compression component inward surface.

30. The probe apparatus of claim 28 in which said bias conveying and signal receiving circuit includes a metal biasing surface formed upon said crystal support surface and in compressively abutting contact with said crystal detector inwardly disposed face.

31. The probe apparatus of claim 30 including:

a treatment circuit mounted upon said crystal support and in electrical communication with said metal biasing surface for electrically treating said detector output to provide output signals corresponding therewith.

32. The probe apparatus of claim 31 in which said metal biasing surface and said treatment circuit comprise a printed circuit including a preamplifier network deriving said output signals.

33. The probe apparatus of claim 28 in which said retainer and grounding assembly inwardly disposed electrical grounding surface comprises a thin coated metal surface.

34. Probe apparatus for locating a source of radiation emission in tissue, comprising:

a hand grippable base portion;

an elongate accessing tube extending from said base portion to a tip region with an internal surface defining a side looking tip region cavity extending to a generally rectangular periphery, said tip region cavity being enclosed at said periphery by a radiation transmissive side-looking window having an internally disposed window surface;

a mounting component within said tip region cavity, having side portions defining a mount cavity with side portions extending to a generally rectangular mount peripheral edge in spaced adjacency with said internally disposed window surface and defining a side opening mount cavity;

a rigid crystal support formed of electrically insulative material, rigidly mounted within said mount cavity, configured having an inwardly disposed surface, an elongate generally rectangular periphery with oppositely disposed side edges at least coextensive with said mount cavity and defining an outwardly disposed crystal support surface;

including an electrically grounded metal surface formed upon said crystal support inwardly disposed surface adjacent a said side edge;

a crystal detector having an outwardly disposed face adjacent said mount peripheral edge and an opposite, inwardly disposed face positioned upon said crystal support surface, and responsive to radiation passing through said window to provide a detector output;

a bias conveying and signal receiving circuit in electrical communication with said crystal detector inwardly disposed face;

a retainer and grounding assembly including a resilient, inwardly biased compression component with an inwardly disposed electrical grounding surface comprising a thin coated metal surface, positioned in abutting compressive relationship over said crystal detector outwardly disposed face and having integrally formed side portions extending with said electrical grounding surface to a dog structure engaging said crystal retainer oppositely disposed side edges to derive said compressive relationship, and said dog structure is abuttably, electrically engaged with said grounded metal surface adjacent said side edge.

35. The probe apparatus of claim 34 including:

a treatment circuit mounted upon said crystal support and having integrator stage components;

said retainer and grounding assembly compression component is configured as a generally U-shaped channel member extending over said crystal detector outwardly disposed face and in electrical shielding relationship over said integrator stage components.

36. Probe apparatus for detecting and locating sources of radiation emission, comprising:

a housing assembly extending from a hand grippable region to a tip region, said tip region having a substantially flat radiation transmission window and an internal surface defining a tip region cavity;

a mounting component formed of material attenuating said radiation mounted within said tip region cavity, having side portions defining a mount cavity with an outwardly disposed peripheral edge in spaced adjacency with said window;

a rigid crystal support formed of electrically insulative material, having an outward surface and an oppositely disposed inward surface extending to a peripheral edge, said crystal support being rigidly mounted within said mount cavity;

an electrically grounded metal surface formed upon said crystal support inward surface adjacent said peripheral edge;

a crystal detector having an outwardly disposed face adjacent to said mount peripheral edge and an oppositely disposed inward surface abuttably positioned and supported upon said crystal support outward surface, and responsive to said radiation emission to provide a detector output;

a bias conveying and signal receiving circuit in electrical communication with said crystal detector inwardly disposed face; and a retainer and grounding assembly including a resilient, inwardly biased compression component having an inward electrical grounding surface positioned in compressive relationship over said crystal detector and having an integrally formed side portion extending to a dog structure abuttably engaging said grounded metal surface at said crystal support to derive said compressive relationship, said dog structure being electrically engaged with said grounded metal surface.

37. The probe apparatus of claim 36 in which said bias conveying and signal receiving circuit includes a treatment circuit having an initial charge accumulating stage of a preamplifier circuit; and said retainer and grounding assembly electrical grounding surface extends over said initial charge accumulating stage.

\* \* \* \* \*